(12) United States Patent
Belau et al.

(10) Patent No.: US 7,851,666 B2
(45) Date of Patent: Dec. 14, 2010

(54) COMPONENTS OF ARTICLES INCLUDING CONTRASTING PRINTED BLOCKS

(75) Inventors: Tom Russell Belau, Neenah, WI (US); Robert David Forrester, Appleton, WI (US); Michael John Flattum, Appleton, WI (US); Paula Cardinahl Winkel, Chilton, WI (US); Bernhardt Edward Kressner, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1227 days.

(21) Appl. No.: 10/452,033

(22) Filed: May 30, 2003

(65) Prior Publication Data

US 2003/0233081 A1    Dec. 18, 2003

Related U.S. Application Data

(60) Provisional application No. 60/387,102, filed on Jun. 7, 2002.

(51) Int. Cl.
*A61F 13/15* (2006.01)
*A61F 13/20* (2006.01)

(52) U.S. Cl. .................. 604/358; 604/362; 604/365; 604/367; 604/378; 604/382; 604/385.01; 604/385.04; 604/385.21; 604/385.23; 604/385.24; 604/385.27; 604/385.3; 604/389; 604/390; 604/394

(58) Field of Classification Search .............. 604/361, 604/317, 385.01, 358, 362, 365, 367, 368, 604/385.04, 385.21, 385.23, 385.24, 385.27, 604/385.3, 389, 390, 394; D24/124; 428/199, 428/187, 32.16
See application file for complete search history.

(56) References Cited

U.S. PATENT DOCUMENTS

| 4,663,220 A | | 5/1987 | Wisneski et al. |
|---|---|---|---|
| 4,945,252 A | | 7/1990 | Lerner et al. |
| 5,197,958 A | * | 3/1993 | Howell ............... 604/361 |
| 5,226,992 A | | 7/1993 | Morman |
| 5,235,515 A | * | 8/1993 | Ungpiyakul et al. ....... 700/125 |
| 5,286,543 A | | 2/1994 | Ungpiyakul et al. |
| D352,779 S | * | 11/1994 | Imbro et al. ............... D24/126 |
| 5,411,636 A | | 5/1995 | Hermans et al. |
| 5,575,782 A | * | 11/1996 | Hasse et al. ............ 604/385.21 |
| 5,642,442 A | | 6/1997 | Morton et al. |
| 5,695,868 A | | 12/1997 | McCormack |
| 5,843,056 A | | 12/1998 | Good et al. |

(Continued)

FOREIGN PATENT DOCUMENTS

EP    0 217 032 A2    4/1987

(Continued)

*Primary Examiner*—Tatyana Zalukaeva
*Assistant Examiner*—Adam Marcetich
(74) *Attorney, Agent, or Firm*—David J. Arteman; Bryan R. Rosiejka

(57) ABSTRACT

The present invention relates to disposable absorbent articles including one or more discrete components. Representative discrete components include the nonwoven layer of the outer cover, the absorbent core, the bodyside liner, fasteners, ears and attachment panels. The discrete components include a material having a Surface Topographic Variance value of 30 micrometers or greater. The material includes a printed block having a Printed Block Sensor Value that is about three times greater than a Sensor Value for the area of the material outside of the printed block.

14 Claims, 9 Drawing Sheets

U.S. PATENT DOCUMENTS

| | | | |
|---|---|---|---|
| 5,853,405 A * | 12/1998 | Suprise | 604/391 |
| 5,858,515 A | 1/1999 | Stokes et al. | |
| 6,027,820 A | 2/2000 | O'Hagan et al. | |
| 6,033,502 A * | 3/2000 | Coenen et al. | 156/64 |
| 6,149,934 A | 11/2000 | Krzysik et al. | |
| 6,297,424 B1 * | 10/2001 | Olson et al. | 604/361 |
| 6,352,528 B1 * | 3/2002 | Weber et al. | 604/385.03 |
| 6,354,984 B1 | 3/2002 | Hensley et al. | |
| 6,387,085 B1 * | 5/2002 | Van Gompel et al. | 604/391 |
| 6,552,245 B1 | 4/2003 | Roessler et al. | |
| 6,558,499 B1 | 5/2003 | Pargass et al. | |
| 6,596,918 B1 | 7/2003 | Wehrle et al. | |
| 2001/0044611 A1 * | 11/2001 | Noda et al. | 604/367 |

FOREIGN PATENT DOCUMENTS

| | | |
|---|---|---|
| JP | 57-93154 A | 6/1982 |
| WO | WO 99/32164 A1 | 7/1999 |
| WO | WO 99/32384 A1 | 7/1999 |
| WO | WO 99/32385 A1 * | 7/1999 |
| WO | WO 00/45767 A1 | 8/2000 |
| WO | WO 01/56525 A1 | 8/2001 |
| WO | WO 02/03900 A1 | 1/2002 |
| WO | WO 02/34184 A1 | 5/2002 |

* cited by examiner

COMPONENTS OF ARTICLES INCLUDING CONTRASTING PRINTED BLOCKS

This patent application is a non-provisional patent application claiming priority to U.S. provisional patent application serial No. 60/387,102 filed on Jun. 7, 2002.

BACKGROUND OF THE INVENTION

Disposable absorbent articles such as infant diapers, training pants, feminine care pads and adult incontinence pads/garments are complex products. These types of articles include multiple components, are made on high speed production lines, need to be cost affordable and most importantly, must perform their intended function. In order to be of the quality expected by consumers, individual articles need to include a complete set of the individual components (e.g. an absorbent pad, pair of leg elastics, pair of containment flaps, etc.). Manufacturing systems have been developed that bring all of the components together in one "web" of materials from which individual articles are formed. The quality of the individual articles is controlled so that each article has the intended components and the components are properly attached to and aligned with each other, with some tolerance for manufacturing variability.

In addition to having all of the functional components, consumers expect absorbent articles to be aesthetic, easy to use and comfortable. With some absorbent articles, particularly infant diapers and training pants, one aspect of the product aesthetics has been graphics. Graphics have been used on different components of the articles in order to label the article's brand, size and fit and to provide pictures that are pleasing to caregivers and to children. For example, graphics have been used on the outer covers and the fastener attachment panels of such articles. In some cases, the graphics are "random", meaning they have a repeating pattern that may be cut at any point, similar to wallpaper. A "random" graphic typically begins and ends on a component of an article in such a way that one or more graphic images around the periphery of the component are incomplete or "cut off". More specifically, a graphic may be considered "random" if the component on which the graphic appears may be indiscriminately cut when it is incorporated into the absorbent article. In recent years, the state of the art has developed so that "whole" or "complete" graphics may be provided on individual components of absorbent articles, such as the outer cover and the fastener attachment panel. Such "whole"/"complete"/"intact" graphics are known to those of skill in the art as "registered" graphics. The graphics are referred to as "registered" because the component on which the graphics are printed is registered (during manufacture) with the other components of the article so that the graphics are complete on each individual article.

U.S. Pat. No. 5,286,543 issued on Feb. 15, 1994 to Ungpiyakul et al. describes a method and apparatus for controlling the cutting and placement of components on a moving substrate, where the moving substrate may be a web of materials for forming absorbent articles. U.S. Pat. No. 5,286,543 also describes an article including a backsheet layer, a substantially liquid permeable topsheet layer disposed in an adjacent facing relation with said backsheet layer and an absorbent pad sandwiched between the topsheet and backsheet layers. The article also includes a patch of web material secured to the backsheet layer where the patch includes a reference marker and a set of graphics. The reference marker provides for a selected separating of a set of graphics from a series of interconnected graphic sets. U.S. Pat. No. 5,286,543 describes that the reference marker may include a sequence of dots, dashes or other machine-recognizable patterns. Further, U.S. Pat. No. 5,286,543 describes that the reference marker may include a physical discontinuity, magnetic discontinuity, electrical discontinuity, electromagnetic discontinuity or a combination of such discontinuities. U.S. Pat. No. 5,286,543 also describes that the reference marker can include discrete areas of optical brightener ("OB") material that define or otherwise indicate the desired boundaries of individual patches of web material. One of the examples of individual patches of web material disclosed in U.S. Pat. No. 5,286,543 is a refastenable tape landing zone. U.S. Pat. No. 5,286,543 discloses that suitable web materials for refastenable tape landing zones include polyester, oriented polypropylene, and unoriented polypropylene.

Additional disclosures relating to registration systems have been made. For example, International Publication Number WO 01/56525 A1 relates to a registration system for phasing simultaneously advancing webs of material having variable pitch lengths. International Publication Number WO 01/56525 A1 describes that the position of preprinted objects on a web of material can be established by sensing a visible timing mark on a part of a web that is later removed, sensing a normally invisible to the human eye registration mark that may or may not remain a part of the final product, or using a grid of sensors to look for a recognized pattern of light diffusion.

Disposable absorbent articles have been sold that have included registered graphics. Kimberly-Clark Corporation (Neenah, Wis.) has sold HUGGIES Supreme disposable diapers and PULL-UPS disposable training pants including registered graphics on the film layers of the outer covers. The registration of graphics on Kimberly-Clark products is performed using a reference marker as described in U.S. Pat. No. 5,286,543. The Procter & Gamble Company (Cincinnati, Ohio) has sold PAMPERS disposable diapers including registered graphics on the film layers of the fastener attachment panels. The registration of graphics on Procter & Gamble products appears to be performed using a reference marker that is a rectangular block of deeper color intensity than the colors surrounding the block. Manufacturers of disposable absorbent articles have also sold products including random graphics. For example, Kimberly-Clark Corporation has sold HUGGIES Ultratrim disposable diapers including random graphics on the pattern unbonded nonwoven material (hereinafter referred to as "PUB nonwoven material") that forms the fastener attachment panel. The random graphics printed on the PUB nonwoven material of the fastener attachment panel of HUGGIES Ultratrim disposable diapers included multiple colors juxtaposed with each other.

Fibrous nonwoven materials are very different from film and film-like materials in terms of what kind of surface they provide for printing. For example, nonwoven materials have three-dimensional microstructures and therefore, the nonwoven materials present irregular surfaces for printing. Additionally, nonwoven materials are porous and when ink is printed onto the nonwoven materials, the ink may soak through the nonwoven fibers. Nonwoven materials also have inherent irregularity because of variability in the formation of the polymer fibers. When nonwoven fibers are printed on, the ink must coat the individual fibers.

Considering the challenges associated with printing on nonwoven materials, the known techniques for registering printed graphics may not be optimal. For example, in order to provide a discrete area of a reference marker, such as an optical brightener, a relatively intense concentration of the marker material may need to be applied to the nonwoven material, resulting in higher overall product cost.

SUMMARY OF THE INVENTION

The present invention relates to disposable absorbent articles that include one or more discrete components. The disposable absorbent articles have a longitudinal direction and a lateral direction. Representative discrete components include the outer cover, the absorbent core, the bodyside liner, the fasteners, the ears to which the fasteners may be attached and the attachment panel. The discrete components may be formed of nonwoven, absorbent or other materials, such as knitted loop materials, prior to their introduction to an absorbent article manufacturing line. The material of the discrete component may have three-dimensional topography that is represented by a Surface Topographic Variance value. The Surface Topographic Variance value may also be representative of the irregularity of the surface of the material. The method used to measure the Surface Topographic Variance value is described as part of the detailed description herein. As an example, the material may have a Surface Topographic Variance value of at least 30 micrometers.

The material of the discrete component may include a printed block. The printed block may be located in a longitudinal position on the discrete component and in a lateral position on the discrete component. Because the discrete component is part of the disposable absorbent article, the longitudinal and lateral directions of the discrete component and the article are the same. The printed block may have a Printed Block Sensor Value that is a numerical value that is provided by a sensor in response to detection of the printed block by the sensor. The material of the discrete component may have a Background Sensor Value that is a numerical value that is provided by a sensor in response to detection of the material of the discrete component (except for the area in which the printed block is located) by the sensor. The Background Sensor Value of the material is the Sensor Value of the material of the discrete component in the same lateral position on the discrete component as the printed block. The Printed Block Sensor Value is at least 3.25 times greater than the Background Sensor Value. Therefore, the ratio of the Printed Block Sensor Value to the Background Sensor Value is at least 3.25 to 1.

More specifically, the printed block may have a Printed Block Sensor Value of at least 650 and the material may have a Background Sensor Value of about 200 when a sensor that provides numerical values of similar scale to a RGB Digital Fiberoptic Sensor available from Keyence Corporation (e.g. sensor head part number CZ40/ amplifier part number CZ-K1P) is employed. Further, the printed block may have a Printed Block Sensor Value of at least 950 and the material may have a Background Sensor Value of about 200. The greater the numerical difference between the Printed Block Sensor Value and the Background Sensor Value, the better the detection of the printed block and the better the ability to control the discrete component registration process. The printed block may have a length in the longitudinal direction of the article (and equivalently in the longitudinal direction of the discrete component) of at least 3 millimeters. Further, the printed block may have a length in the lateral direction of the article (and equivalently in the lateral direction of the discrete component) of at least 15 millimeters. The material of the discrete component may include two or more printed blocks.

The material of the discrete component may also include a continuous detector material and a masking block. The masking block is capable of covering up or decreasing the detectable presence of the continuous detector material. The continuous detector material may include an optical brightener material that fluoresces under ultraviolet or another wavelength range of light. The masking block may include an opaque printed ink.

When the discrete component is the outer cover of the article, the outer cover may include a spunbond nonwoven material and the outer cover may have a Surface Topographic Variance value of at least 30 micrometers. When the discrete component is the attachment panel of the article, the attachment panel may include a pattern unbonded nonwoven material that has a Surface Topographic Variance value of at least 200 micrometers. The pattern unbonded nonwoven material may have a basis weight of 1.0 to 2.5 ounces per square yard. The discrete component of the disposable absorbent article may also include a necked bonded laminate material that has a Surface Topographic Variance value of at least 125 micrometers. An example of a discrete component that may include a necked bonded laminate material is the ears that are attached to the longitudinal edges of the article in either the back waist region or the front waist region.

In another aspect, the present invention relates to a disposable absorbent article that includes a longitudinal direction and a lateral direction. The longitudinal direction relates generally to the length dimension of the article. When the article is a disposable infant diaper, the longitudinal direction runs in the direction of the length of the diaper from the back waist region to the front waist region. The lateral direction relates generally to the width dimension of the article. The lateral direction is generally perpendicular to the longitudinal direction. The disposable absorbent article includes an outer cover, a bodyside liner and an absorbent core located between the outer cover and the bodyside liner. The outer cover may include a nonwoven material and the outer cover may have a Surface Topographic Variance value of at least 30 micrometers. The nonwoven material may include a printed block. The printed block may be located in a longitudinal position on the outer cover and in a lateral position on the outer cover. The printed block may have a Printed Block Sensor Value and the nonwoven material may have a Background Sensor Value at the same lateral position as the printed block. The Printed Block Sensor Value may be at least 3.25 times greater than the Background Sensor Value such that a ratio of the two Values is at least 3.25 to 1.

The nonwoven material may include a printed picture. The printed picture may include objects, letters, numbers, symbols or illustrations. When the Sensor Values are measured by a sensor similar to a RGB Digital Fiberoptic Sensor available from Keyence Corporation (e.g. sensor head part number CZ40/ amplifier part number CZ-K1P), the printed block may have a Printed Block Sensor Value of at least 650 and the nonwoven material may have a Background Sensor Value of about 200. More specifically, the printed block may have a Printed Block Sensor Value of at least 950 and the nonwoven material may have a Background Sensor Value of about 200. The printed block may have a length in the longitudinal direction of the outer cover of at least 3 millimeters. Further, the printed block may have a length in the lateral direction of the outer cover of at least 15 millimeters. The nonwoven material of the outer cover may include two or more printed blocks. The printed blocks may be separated from each other in such a way that the nonwoven material of the outer cover having the Background Sensor Value is in between them.

The outer cover may further include a continuous detector material and a masking block. The continuous detector material may be an optical brightener and the optical brightener may have a concentration of from 0.1% to 2.5% in the nonwoven material of the outer cover. The masking block may have a length in the longitudinal direction of the outer cover of at least 3 millimeters. The masking block may also have a length in the lateral direction of the outer cover of at least 13 millimeters. The masking block may include an opaque printed ink.

In another aspect, the present invention relates to a disposable absorbent article having a longitudinal direction and a lateral direction. The disposable absorbent article may include an outer cover having a garment-facing surface, a bodyside liner and an absorbent core located between the outer cover and the bodyside liner. The garment-facing surface of the outer cover is the surface of the outer cover that faces away from the user's skin and may be in proximity to the wearer's clothes or garments. The disposable absorbent article may also include an attachment panel and the attachment panel may be located on the garment-facing surface of the outer cover. The attachment panel may include a nonwoven material and the nonwoven material may have a Surface Topographic Variance value of at least 30 micrometers. The nonwoven material may include a printed block. The printed block may be located in a longitudinal position on the attachment panel and in a lateral position on the attachment panel. The printed block may have a Printed Block Sensor Value and the nonwoven material may have a Background Sensor Value at the same lateral position as the printed block. The Printed Block Sensor Value may be at least 3.25 times greater than the Background Sensor Value such that a ratio of the two Values is at least 3.25 to 1.

The attachment panel may include a printed picture. The attachment panel may also include a nonwoven material that has a Surface Topographic Variance value of at least 175. More specifically, the attachment panel may include a pattern unbonded nonwoven material having a Surface Topographic Variance value of at least 200. When the Sensor Values are measured by a sensor similar to a RGB Digital Fiberoptic Sensor available from Keyence Corporation (e.g. sensor head part number CZ40/ amplifier part number CZ-K1P), the printed block may have a Printed Block Sensor Value of at least 650 and the nonwoven material may have a Background Sensor Value of about 200. More specifically, the printed block may have a Printed Block Sensor Value of at least 950 and the nonwoven material may have a Background Sensor Value of about 200. The printed block may have a length in the longitudinal direction of the attachment panel of at least 3 millimeters. Further, the printed block may have a length in the lateral direction of the attachment panel of at least 15 millimeters. The nonwoven material of the attachment panel may include two or more printed blocks. The printed blocks may be separated from each other in such a way that the nonwoven material of the attachment panel having the Background Sensor Value is in between them.

The attachment panel may include a continuous detector material and a masking block. The continuous detector material may be an optical brightener and the optical brightener may have a concentration of from 0.5% to 2.5% in the nonwoven material of the attachment panel. The masking block may have a length in the longitudinal direction of the attachment panel of at least 3 millimeters. The masking block may have a length in the lateral direction of the attachment panel of at least 13 millimeters. The masking block may include an opaque printed ink.

In another aspect, the present invention relates to a disposable absorbent article having a longitudinal direction and a lateral direction including an outer cover, a bodyside liner and an absorbent core located between the outer cover and the bodyside liner. The outer cover may have a garment-facing surface. The outer cover may include a nonwoven material and the outer cover may have a Surface Topographic Variance value of at least 30 micrometers. The nonwoven material may include an outer cover printed block. The outer cover printed block may be located in a longitudinal position on the outer cover and in a lateral position on the outer cover. The outer cover printed block may have a Printed Block Sensor Value and the nonwoven material may have a Background Sensor Value at the same lateral position as the outer cover printed block. The Printed Block Sensor Value may be at least 3.25 times greater than the Background Sensor Value such that a ratio of the two Values is at least 3.25 to 1. The disposable absorbent article may also include an attachment panel and the attachment panel may be located on the garment-facing surface of the outer cover. The attachment panel may include an attachment nonwoven material and the attachment nonwoven material may have a Surface Topographic Variance value of at least 30 micrometers. The attachment nonwoven material may include an attachment panel printed block. The attachment panel printed block may be located in a longitudinal position on the attachment panel and in a lateral position on the attachment panel. The attachment panel printed block may have a Printed Block Sensor Value and the attachment nonwoven material may have a Background Sensor Value at the same lateral position as the attachment panel printed block. The Printed Block Sensor Value may be at least 3.25 times greater than the Background Sensor Value such that a ratio of the two Values is at least 3.25 to 1. In this aspect of the invention, the disposable absorbent article includes both an outer cover printed block and an attachment panel printed block.

It is to be understood that both the foregoing general description and the following detailed description are exemplary and are intended to provide further explanation of the invention claimed. The accompanying drawings, that are incorporated in and constitute part of this specification, are included to illustrate and provide a further understanding of the articles of the invention. Together with the description, the drawings serve to explain various aspects of the invention.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The present invention is directed to solving problems related to absorbent articles including components that are registered in relation to each other and to absorbent articles including registered graphics. Additionally, the present invention is directed to solving problems associated with registration on materials having irregular surfaces. This detailed description of the present invention will include a description of a representative absorbent article including the various components of such articles. The description of the representative absorbent article will also include a description of the features encompassed by the present invention. Subsequent to the description of the representative absorbent article, a representative registration system will be described.

Representative Absorbent Article

The absorbent articles of the present invention will be described in terms of a disposable diaper article that is adapted to be worn by infants about the lower torso. It is understood that the features of the present invention are equally adaptable for other types of absorbent articles such as adult incontinence pads, adult incontinence garments, training pants, disposable swim pants, feminine hygiene pads and prefastened or refastenable diaper pants.

Figure 1:
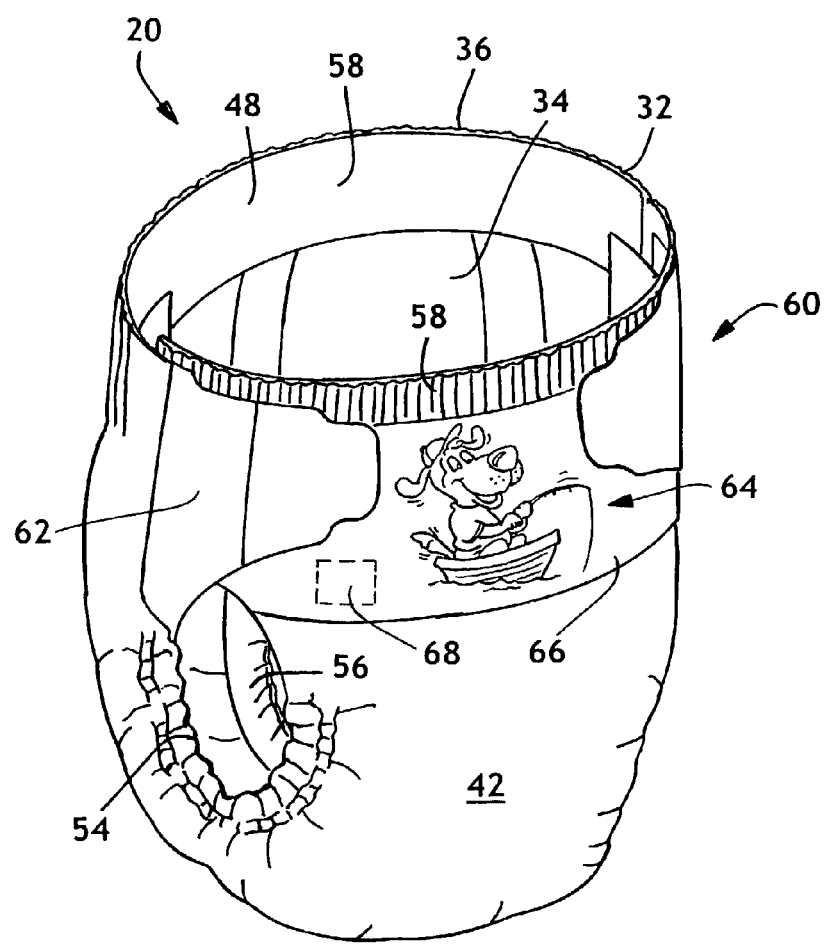
FIG. 1 representatively shows a perspective view of an example of a disposable absorbent article of the present invention.
Figure 2:
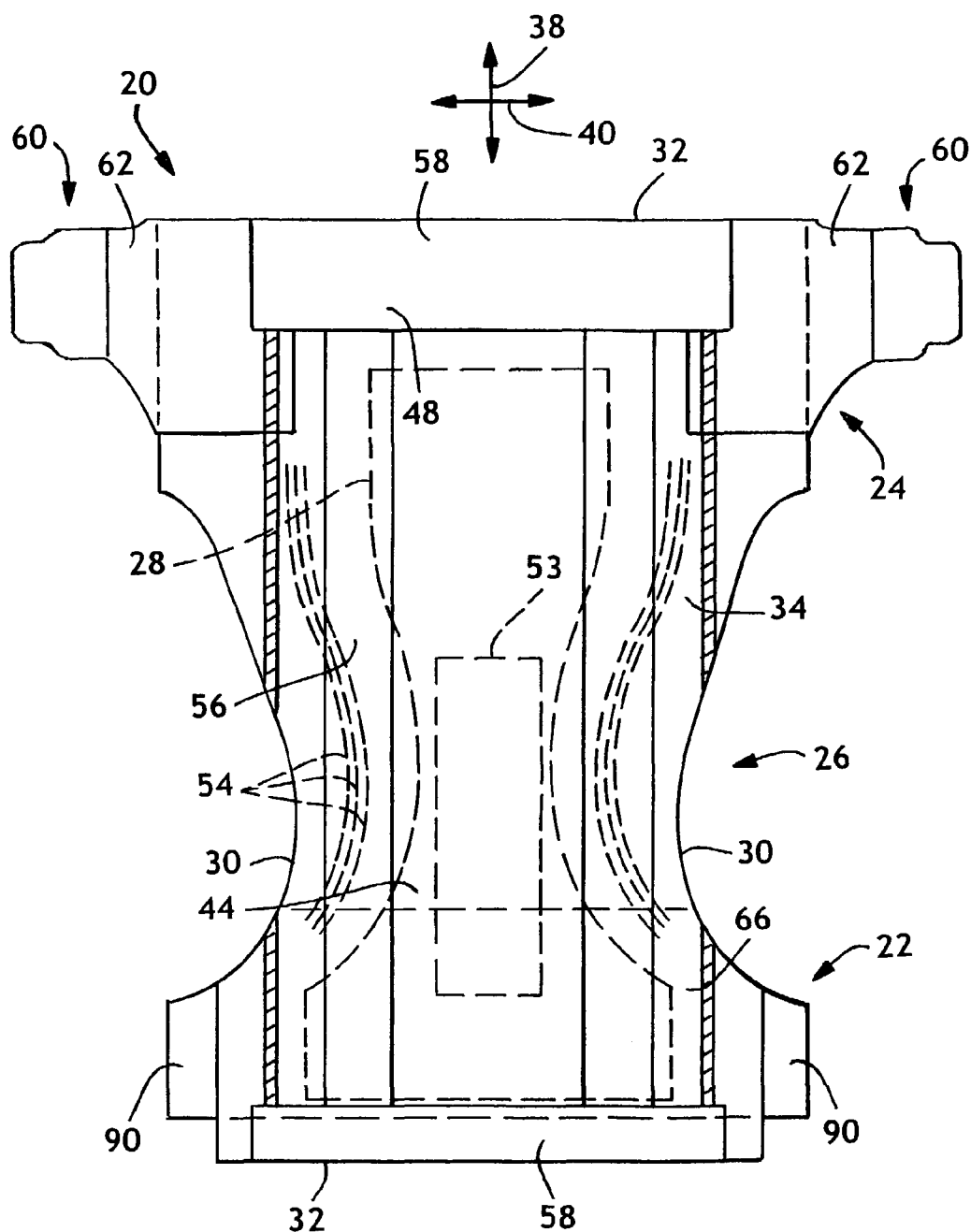
FIG. 2 representatively shows a plan view of the disposable absorbent article of FIG. 1 in an unfastened, stretched and laid flat condition with the surface of the article which contacts the wearer's skin facing the viewer and with portions of the article partially cut away to show the underlying features.

FIG. 1 representatively illustrates an example of a refastenable disposable diaper, as generally indicated at 20, of the present invention. FIG. 2 representatively illustrates the refastenable diaper of FIG. 1 in an unfastened, stretched and laid flat configuration with the surface of the diaper adapted to contact the wearer's skin facing the viewer and with portions of the diaper partially cut away to show the underlying features. As illustrated in FIG. 2, the diaper 20 defines a front waist region 22, a back waist region 24, a crotch region 26 that extends between and connects the front and back waist regions 22 and 24, a longitudinal direction 38 and a lateral direction 40. The front waist region 22 includes the portion of the diaper 20 that, when worn, is positioned on the front of the wearer while the back waist region 24 includes the portion of the diaper 20 that, when worn, is positioned on the back of the wearer. The crotch region 26 of the diaper 20 includes the portion of the diaper 20 that, when worn, is positioned between the legs of the wearer and covers the lower torso of the wearer.

The diaper 20 defines a pair of laterally opposed side edges 30, a pair of longitudinally opposed waist edges 32, an interior surface 34 that is configured to contact the wearer, and an exterior surface 36 opposite the interior surface 34 that is configured to contact the wearer's clothing in use. The illustrated diaper 20 also includes a substantially liquid impermeable outer cover 42 and a liquid permeable bodyside liner 44 that can be connected to the outer cover 42 in a superposed relation. An absorbent core 28 is located between the outer cover 42 and the bodyside liner 44. The laterally opposed side edges 30 of the diaper 20 are generally defined by the side edges of the outer cover 42 that further define leg openings that may be curvilinear. The waist edges 32 of the diaper 20 are generally defined by the waist edges of the outer cover 42 and define a waist opening that is configured to encircle the waist of the wearer when worn. The absorbent core 28 is configured to contain and/or absorb body exudates discharged from the wearer. The diaper 20 may further include leg elastics 54, containment flaps 56 and waist elastics 58 as are known to those skilled in the art. It should be recognized that individual components of the diaper 20 may be optional depending upon the intended use of the diaper 20.

The diaper 20 can further include refastenable mechanical fasteners 60. The mechanical fasteners 60 releasably engage the opposed side edges 30 of the diaper 20 in the opposite waist regions. The mechanical fasteners 60 can include a variety of materials and surfaces known for mechanical engagement such as buttons, pins, snaps, adhesive tape fasteners, cohesives, mushroom-and-loop fasteners and hook and loop fasteners. Further, the disposable diaper 20 may include an attachment panel 66 located on the front or back waist region 22 and 24, opposite the fasteners 60 to which the fasteners 60 can be releasably engaged during use of the diaper 20.

The diaper 20 may be of various suitable shapes. For example, in the unfastened configuration as illustrated in FIG. 2, the diaper 20 may have an overall rectangular shape, T-shape or an approximately hourglass shape. In the shown embodiment, the diaper 20 has a generally I-shape in an unfastened configuration.

The various components of the diaper 20 are integrally assembled together employing various types of suitable attachment means, such as adhesive, sonic and thermal bonds or combinations thereof. In the shown embodiment, for example, the outer cover 42 and bodyside liner 44 are assembled to each other and to the absorbent core 28 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Alternatively, the absorbent core 28 may be connected to the outer cover 42 using conventional fasteners such as buttons, hook and loop type fasteners, adhesive tape fasteners, and the like. The other components of the diaper 20 may be suitably connected together using similar means. Similarly, other diaper components, such as the elastic members 54 and 58 and the mechanical fasteners 60, may be assembled into the diaper 20 article by employing the above-identified attachment mechanisms. Desirably, the majority of the diaper components are assembled together using ultrasonic bonding techniques for reduced manufacturing cost.

The outer cover 42 of the diaper 20, as representatively illustrated in FIGS. 1-2, may suitably be composed of a material which is either liquid permeable or liquid impermeable. It is generally preferred that the outer cover 42 be formed from a material that is substantially impermeable to liquids. A typical outer cover can be manufactured from a thin plastic film or other flexible liquid-impermeable material. For example, the outer cover 42 may be formed from a polyethylene film having a thickness of from about 0.013 millimeter (0.5 mil) to about 0.051 millimeter (2.0 mils). The materials of the outer cover 42 can be thermally or adhesively laminated together. Suitable laminate adhesives, which can be applied continuously or intermittently as beads, a spray, parallel swirls, or the like, can be obtained from Bostik-Findley, Inc., of Wauwatosa, Wis., U.S.A., or from National Starch and Chemical Company, Bridgewater, N.J., U.S.A. If it is desired to present the outer cover 42 with a more clothlike feeling, the outer cover 42 may be formed from a polyolefin film having a nonwoven web laminated to the exterior surface thereof, such as a spunbond web of polyolefin fibers. For example, a stretch-thinned polypropylene film having a thickness of about 0.015 millimeter (0.6 mil) may be thermally laminated thereto a spunbond web of polypropylene fibers. The polypropylene fibers may have a fiber diameter of about 15 to 20 microns; which nonwoven web has a basis weight of about 17 grams per square meter (0.5 ounce per square yard). The outer cover 42 may include bicomponent fibers such as polyethylene/polypropylene bicomponent fibers. Methods of forming such clothlike outer covers are known to those skilled in the art. The outer cover 42 may also be an extensible outer cover such as the outer covers described in U.S. Patent No. 6,552,245 issued on Apr. 22, 2003 to Roessler et al. The outer cover 42 can also be a biaxially stretchable outer cover such as the outer covers described in U.S. patent application Ser. No. 09/698,517 filed on Oct. 27, 2000 by Vukos et al.

The outer cover 42 may be formed of a woven or nonwoven fibrous web layer which has been totally or partially constructed or treated to impart a desired level of liquid impermeability to selected regions that are adjacent or proximate the absorbent core 28. Still further, the outer cover 42 may optionally be composed of a micro-porous "breathable" material which permits vapors to escape from the absorbent core 28 while still preventing liquid exudates from passing through the outer cover 42. For example, the outer cover 42 may include a vapor permeable non-woven facing layer laminated to a micro-porous film. Suitable "breathable" outer cover materials are described in U.S. Pat. No. 5,695,868 issued to McCormack et al. and U.S. Pat. No. 5,843,056 issued Dec. 1, 1998 to Good et al., the descriptions of which are hereby incorporated by reference. Still further, the outer cover 42 may also be an elastomeric material such as a stretch-thermal laminate (STL), neck-bonded laminate (NBL), or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., the disclosures of which are hereby incorporated by reference. The outer cover 42 can also be embossed or otherwise provided with a matte finish to provide a more aesthetically pleasing appearance.

In order to reduce the perception that the outer cover 42 feels damp or clammy, the diapers 20 of the invention may include a spacer or ventilation layer (not shown in Figures) between the garment-facing surface of the absorbent core 28 and the outer cover 42. The ventilation layer may include one or more nonwoven materials, for example a spunbond-meltblown-spunbond nonwoven material.

The representative absorbent articles of the invention include a bodyside liner 44 in superimposed relation to the outer cover 42. The bodyside liner 44, as representatively illustrated in FIG. 2, suitably presents a bodyfacing surface that is compliant, soft feeling, and nonirritating to the wearer's skin. Further, the bodyside liner 44 may be less hydrophilic than the absorbent core 28, to present a relatively dry surface to the wearer, and may be sufficiently porous to be liquid permeable, permitting liquid to readily penetrate through its thickness. A suitable bodyside liner 44 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 44 is suitably employed to help isolate the wearer's skin from liquids held in the absorbent 28. The bodyside liner 44 can also be made from extensible materials as are described in U.S. Patent No. 6,552,245 issued on Apr. 22, 2003 to Roessler at al. The bodyside liner 44 can also be made from biaxially stretchable materials as are described in U.S. patent application Ser. No. 09/698,517 filed on Oct. 27, 2000 by Vukos et al.

Various woven and nonwoven fabrics can be used for the bodyside liner 44. For example, the bodyside liner may be composed of a meltblown or spunbond web of polyolefin fibers. The bodyside liner 44 may also be a bonded-carded web composed of natural and/or synthetic fibers. The bodyside liner 44 may be composed of a substantially hydrophobic material, and the hydrophobic material may optionally be treated with a surfactant or otherwise processed to impart a desired level of wettability and hydrophilicity. In a particular embodiment of the present invention, the bodyside liner 44 is made from a nonwoven, spunbond, polypropylene fabric composed of fibers having a fiber diameter of about 21 to 23 microns formed into a web having a basis weight of about 20 grams per square meter and a density of about 0.13 grams per cubic centimeter. The fabric may be surface treated with about 0.3 weight percent of a surfactant, such as a surfactant commercially available from Hodgson Textile Chemicals, Inc. under the trade designation AHCOVEL Base N-62. The surfactant may be applied by any conventional means, such as spraying, printing, brush coating or similar techniques. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a lotion or treatment applied thereto that is configured to be transferred to the wearer's skin. Suitable compositions for application to the bodyside liner 44 are described in U.S. Pat. No. 6,149,934 that issued to Krzysik et al. on Nov. 21, 2000.

The representative absorbent articles of the invention can include an absorbent core 28 disposed between the outer cover 42 and the bodyside liner 44. The absorbent core 28 of the diaper 20, as representatively illustrated in FIG. 1, may suitably include a matrix of hydrophilic fibers, such as a web of cellulosic fluff, mixed with particles of a high-absorbency material commonly known as superabsorbent material. In a particular aspect, the absorbent core 28 includes a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the absorbent core 28 may include a laminate of fibrous webs and superabsorbent material or other suitable matrix for maintaining a superabsorbent material in a localized area.

The absorbent core 28 may have any of a number of shapes. For example, the absorbent core 28 may be rectangular, I-shaped, or T-shaped. It is generally preferred that the absorbent core 28 is narrower in the intermediate section than in the front or rear waist sections of the diaper 20. The absorbent core 28 may be provided by a single layer or, in the alternative, may be provided by multiple layers, all of which need not extend the entire length and width of the absorbent core 28. In a particular aspect of the invention, the absorbent core 28 can be generally T-shaped with the laterally extending cross-bar of the "T" generally corresponding to the front waist region 22 of the absorbent article for improved performance, especially for male infants.

The size and the absorbent capacity of absorbent core 28 should be compatible with the size of the intended wearer and the liquid loading imparted by the intended use of the absorbent article. Further, the size and the absorbent capacity of the absorbent core 28 can be varied to accommodate wearers ranging from infants through adults. In addition, it has been found that with the present invention, the densities and/or basis weights of the absorbent core 28 can be varied.

The high-absorbency material may be selected from natural, synthetic, and modified natural polymers and materials. The high-absorbency materials may be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in the absorbent core 28 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. In general, the high absorbency material is present in the absorbent core 28 in an amount of from about 5 to about 90 percent by weight, desirably in an amount of at least about 30 percent by weight, and even more desirably in an amount of at least about 50 percent by weight based on a total weight of the absorbent core 28. For example, in a particular aspect, the absorbent core 28 may include a laminate which includes at least about 50 percent by weight and desirably at least about 70 percent by weight of high-absorbency material overwrapped by a fibrous web or other suitable material for maintaining the high-absorbency material in a localized area.

An example of high-absorbency material suitable for use in the present invention is DRYTECH 2035 polymer available from Dow Chemical, a business having offices in Midland, Mich. Other suitable superabsorbents may include FAVOR SXM 880 polymer obtained from Stockhausen, a business having offices in Greensboro, N.C.

Optionally, a substantially hydrophilic tissue or nonwoven wrapsheet (not illustrated) may be employed to help maintain the integrity of the structure of the absorbent core 28. The wrapsheet is typically placed about the absorbent core 28 over at least the two major facing surfaces thereof. The wrapsheet may be composed of an absorbent cellulosic material, such as creped wadding or a high wet-strength tissue. In one aspect of the invention, the wrapsheet may be configured to provide a wicking layer that helps to rapidly distribute liquid over the mass of absorbent fibers constituting the absorbent core 28.

Due to the thinness of absorbent core 28 and the high absorbency material within the absorbent core 28, the liquid uptake rates of the absorbent core 28, by itself, may be too low, or may not be adequately sustained over multiple insults of liquid into the absorbent core 28. To improve the overall liquid uptake and air exchange, the diaper 20 of the different aspects of the present invention may further include a porous, liquid-permeable layer of surge management material 53, as representatively illustrated in FIG. 2. The surge management layer 53 is typically less hydrophilic than the absorbent core 28, and has an operable level of density and basis weight to quickly collect and temporarily hold liquid surges, to transport the liquid from its initial entrance point and to substantially completely release the liquid to other parts of the absorbent core 28. This configuration can help prevent the liquid from pooling and collecting on the portion of the diaper 20 positioned against the wearer's skin, thereby reducing the feeling of wetness by the wearer. The structure of the surge management layer 53 also generally enhances the air exchange within the diaper 20.

Various woven and nonwoven fabrics can be used to construct the surge management layer 53. For example, the surge management layer 53 may be a layer composed of a meltblown or spunbond web of synthetic fibers, such as polyolefin fibers. The surge management layer 53 may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge management layer 53 may be composed of a substantially hydrophobic material, and the hydrophobic material may optionally be treated with a surfactant or otherwise processed to impart a desired level of wettability and hydrophilicity. In a particular aspect, the surge management layer 53 includes a hydrophobic, nonwoven material having a basis weight of from about 30 to about 120 grams per square meter.

The absorbent articles of the invention can include additional components. For example, as representatively illustrated in FIGS. 1 and 2, the disposable diaper 20 may include a pair of containment flaps 56 that are configured to provide a barrier to the lateral flow of body exudates. The containment flaps 56 may be located along the laterally opposed side edges 30 of the diaper adjacent the side edges of the absorbent core 28. Each containment flap 56 typically defines an unattached edge that is configured to maintain an upright, perpendicular configuration in at least the crotch region 26 of the diaper 20 to form a seal against the wearers body. The containment flaps 56 may extend longitudinally along the entire length of the absorbent core 28 or may only extend partially along the length of the absorbent core 28. When the containment flaps 56 are shorter in length than the absorbent core 28, the containment flaps 56 can be selectively positioned anywhere along the side edges 30 of diaper 20 in the crotch region 26. In a particular aspect of the invention, the containment flaps 56 extend along the entire length of the absorbent core 28 to better contain the body exudates. Such containment flaps 56 are generally well known to those skilled in the art.

The diaper 20 of the different configurations of the present invention may further include elastics at the waist edges 32 and side edges 30 of the diaper 20 to further prevent leakage of body exudates and support the absorbent core 28. For example, as representatively illustrated in FIGS. 1-2, the diaper 20 of the present invention may include a pair of leg elastic members 54 that are connected to the laterally opposed side edges 30 of the diaper 20 in the crotch region 26. The diaper 20 may also include a pair of waist elastic members 58 that is connected to the longitudinally opposed waist edges 32 of the diaper 20. The leg elastics 54 and waist elastics 58 are generally adapted to fit about the legs and waist of a wearer in use to maintain a positive, contacting relationship with the wearer to effectively reduce or eliminate the leakage of body exudates from the diaper 20.

Materials suitable for use as the leg elastics 54 and waist elastics 58 are well known to those skilled in the art. Exemplary of such materials are sheets or strands or ribbons of a polymeric, elastomeric material that may be adhered to the outer cover 42 in a stretched position, or that may be attached to the outer cover 42 while the outer cover is pleated, such that elastic constrictive forces are imparted to the outer cover 42. The leg elastics 54 may also include such materials as polyurethane, synthetic and natural rubber.

The diaper 20 of the different configurations of the present invention may further include a fit panel 48 superimposed adjacent to the waist edge 30 in at least one of the waist sections 22 and 24, to provide a more comfortable, contouring fit about the wearer. For example, as illustrated in FIG. 2, the diaper 20 may include a fit panel 48 superimposed adjacent the waist edge 32 on either the interior or exterior surface 34 and 36 of the diaper 20. Or there may be a fit panel located on both surfaces 34 and 36 of the diaper 20 simultaneously. The diaper may include a fit panel disposed in both waist sections 22 and 24, and desirably the diaper may include a fit panel in at least the rear waist section 24. Desirably, the fit panel is extensible or elastomeric. For example, as representatively illustrated in FIG. 2, the diaper 20 can include an elastomeric fit panel 48 on the interior surface 34 of the diaper 20 that is configured to elongate in the lateral direction 40 to provide an improved fit and appearance of the absorbent article about the wearer. This can be accomplished by providing a mechanism for the waist region to expand, thereby increasing the waist perimeter dimension to assist in applying the diaper 20 on the wearer. Desirably the elastomeric or extensible fit panel 48 allows the waist perimeter dimension to expand at least about 20 percent, more desirably at least about 40 percent and even more desirably at least about 50 percent.

An additional component that may be incorporated into the diapers of the invention is laterally-extending ears 62 to which the refastenable mechanical fasteners 60 may be attached. The ears 62 may be attached to the diaper 20 at the side edges 30 using known techniques including ultrasonic bonding. The ears 62 may be constructed of one or more nonwoven materials, including nonwoven materials that are stretchable. The ears 62 may increase the range with which the fasteners may be engaged into the attachment panel 66 or directly into the outer cover 42. An exemplary material from which the ears 62 may be constructed is a necked bonded laminate material having two nonwoven (e.g. spunbond) facings with an elastomeric film (e.g. KRATON film) laminated in between.

Consistent with the description provided so far, absorbent articles are typically made from several layers of nonwoven materials and absorbent materials that are brought together during manufacture. The layered materials may include the outer cover 42, the ventilation layer, the absorbent core 28, the surge management material 53 and the bodyside liner 44. In addition to the layers of materials that may run in generally overlapping relationship to each other, absorbent articles may include components such as ears 62, fasteners 60, leg elastics 54, waist elastics 58, containment flaps 56 and attachment panels 66 that are separately attached to the layered materials. The disposable absorbent articles of the invention may include discrete components that are either the layered materials or the separately attached components. For example, discrete components may include the outer cover laminate 42, the nonwoven component of the outer cover laminate 42, the absorbent core 28, the bodyside liner 44, the ears 62, the fasteners 60 and the attachment panel 66. In an aspect of the invention, it may be desirable for a discrete component to be registered with respect to other components or to provide a picture or graphic that is registered. For example, it may be desirable to register the materials of the absorbent core 28 to a particular position in relation to the outer cover 42. In another example, attachment panel 66 material may be provided to a composite web of materials running on a manufacturing line as a separate web of material. Further with regard to this example, the attachment panel 66 material may include a series of printed graphics or pictures and it may be desirable to provide a portion of the attachment panel 66 material web that includes an intact graphic or picture to the composite web of materials. In this sense, the attachment panel 66 material would be registered with the composite web of materials.

Figure 3:
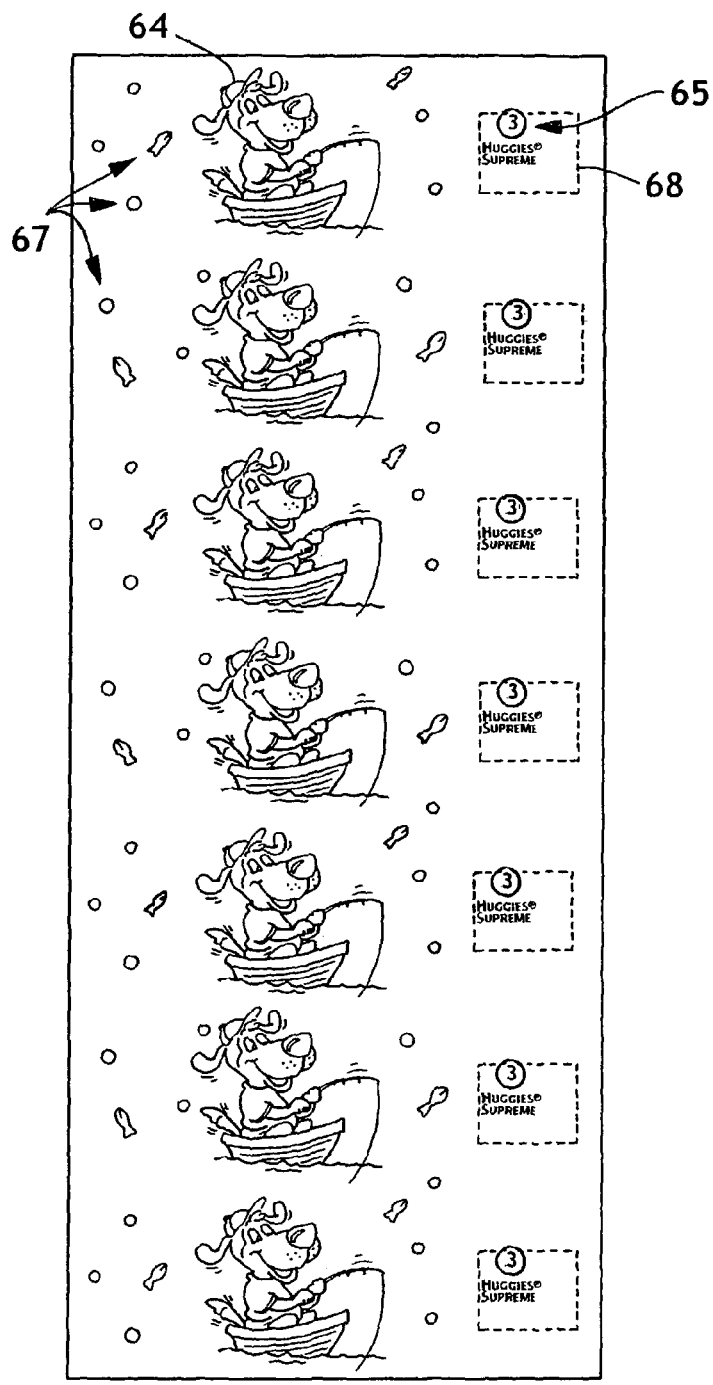
FIG. 3 representatively shows a plan view of an attachment panel web of material from which individual attachment panels may be formed.

The graphics or pictures may include words, text, numbers, cartoon-like characters, objects or illustrations. The graphics or pictures may include a picture that in and of itself may be described as whole, complete or intact. For example, in FIG. 1, the attachment panel 66 includes a picture 64 of a caricature of a dog sitting in a boat. While the picture 64 does not show the end of the fishing pole that the dog is holding or the body of water in which the dog's boat is sitting, the top of the picture 64 does not include the bottom of another boat and the bottom of the picture 64 does not include the hat and ears of another dog. The graphic or picture 64 may also include tradenames or trademarks or other information about the product on which the graphic or picture 64 is appearing. In addition to including an intact picture 64, the discrete component such as an attachment panel 66 may also include repeating or random graphics. For example, FIG. 3 representatively depicts a two dimensional view of an exemplary attachment panel 66 material web that includes a series of graphics or pictures 64 prior to separation and attachment to individual diapers 20. The attachment panel 66 material web shown in FIG. 3 includes a series of pictures 64 and a repeating graphic 67 in the background. Associated with each picture 64 image is also product information 65. Desirable product information 65 may include product brand name, product size or other information concerning use of the diaper 20. Typically, it would be desirable to sever the attachment panel 66 material web shown in FIG. 3 at locations that are in between the pictures 64 and not through the pictures 64. This concept is consistent with the technique known in the art as the registration or controlled placement of components or graphics.

Figure 10:
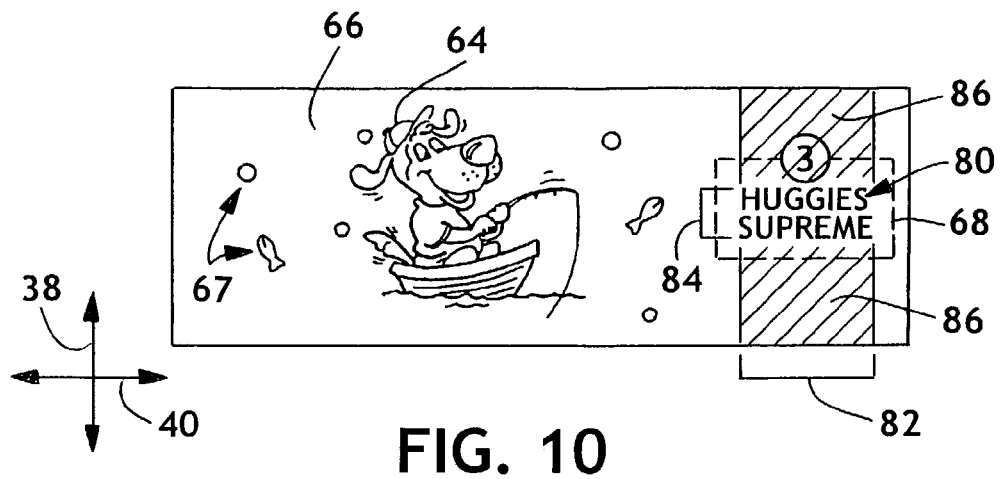
FIG. 10 representatively shows a plan view of an attachment panel that may be used in the disposable absorbent articles of the invention.

The disposable absorbent articles of the invention may include more than one discrete component. The discrete component may include a material, such as a nonwoven material or a knitted loop material. The material may include a printed block 80 as illustrated in FIG. 10. FIG. 10 shows a representative discrete component, an attachment panel 66. As part of the disposable absorbent article 20, the attachment panel has a longitudinal direction 38 and a lateral direction 40 that correspond to the longitudinal direction 38 and the lateral direction 40 of the article 20. The printed block 80 may include a block of printed ink, one or more words, one or more numbers, one or more symbols or one or more objects. Examples of typical objects include pictures or other graphic representations. The printed block 80 is located in a longitudinal position 84 on the discrete component and is located in a lateral position 82 on the discrete component.

When a representative registration system, such as the system described later herein, is used, the printed block 80 may have a Printed Block Sensor Value. The Printed Block Sensor Value is a numerical value that corresponds to a signal detected by a sensor when the printed block 80 is within the physical detection range of the sensor. The material of the attachment panel 66 outside of and surrounding the printed block 80 may also have a sensor value which may be referred to as a Background Sensor Value. The Background Sensor Value is also a numerical value that corresponds to a signal detected by a sensor when the material of the attachment panel 66 is within the physical detection range of the sensor. Desirably, in order for the sensor to distinguish the printed block 80 from the remainder of the material of the attachment panel 66, the printed block 80 has a Sensor Value that is about 3.25 times greater than the Sensor Value for the material surrounding the printed block 80. The Sensor Value for the material of the attachment panel 66 surrounding the printed block 80 that is relevant is the Sensor Value for the material having the same lateral position 86 as the lateral position 82 of the printed block 80. For example, if the longitudinal direction 38 of the diaper 20 corresponds to the direction of manufacture (i.e., the machine direction), the material of the attachment panel 66 would be moving past the sensor in the longitudinal direction 38. Based on the position of the printed block 80 illustrated in FIG. 10, as the attachment panel material moved past the sensor, the sensor would first react to the Background Sensor Value of the material 86 having the same lateral position as that of the printed block 80. As the material moved along, the upper edge of the printed block 80 would then pass by the sensor and the sensor would react to the Printed Block Sensor Value of the printed block 80. Subsequently, the lower edge of the printed block 80 would pass by the sensor and the sensor would react to a shift from the Printed Block Sensor Value to the Background Sensor Value. With the example provided in FIG. 10, the printed block 80 appears near a lateral edge of the attachment panel 66. The printed block 80 may appear in any location on the attachment panel 66, including within the picture 64 or the repeating graphic 67.

A representative sensor that may be used to detect the presence of a printed block 80 is a RGB Digital Fiberoptic Sensor such as those manufactured by Keyence Corporation having an office in Schaumberg, Ill. A specific example of a Keyence RGB Digital Fiberoptic Sensor is a CZ-K1P series sensor (part number CZ40 is the sensor head and part number CZ-K1P is the amplifier). Using this type of sensor, the printed block 80 may have a Printed Block Sensor Value of about 650 or greater and the surrounding material of the attachment panel 66 may have a Background Sensor Value of about 200. Desirably, to improve the quality of registration and to account for process variability, the printed block 80 may have a Printed Block Sensor Value of about 950 or greater and the surrounding material of the attachment panel 66 may have a Background Sensor Value of about 200.

Figure 11:
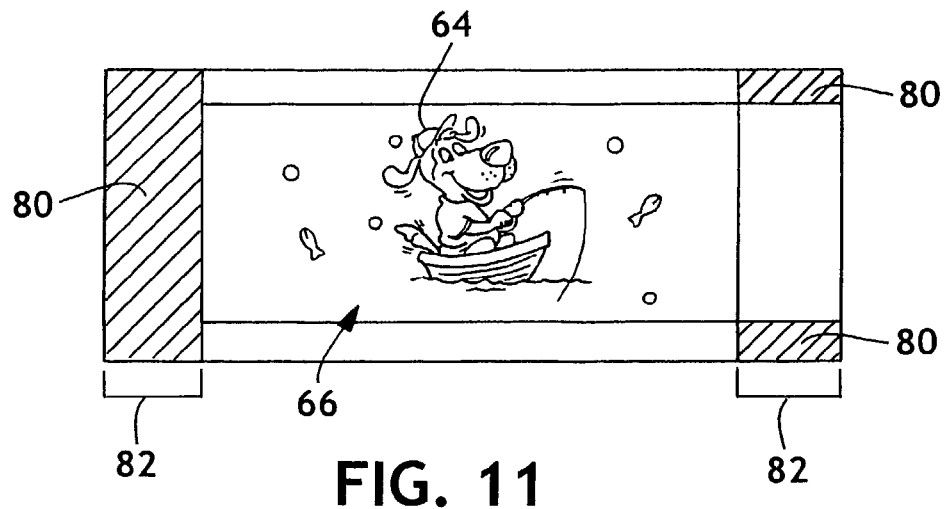
FIG. 11 representatively shows a plan view of an attachment panel that may be used in the disposable absorbent articles of the invention.
Figure 12:
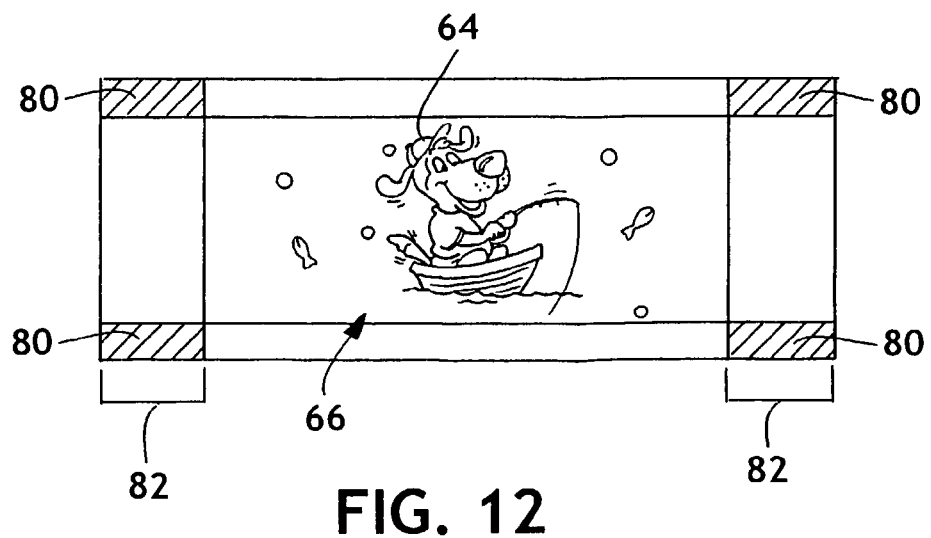
FIG. 12 representatively shows a plan view of an attachment panel that may be used in the disposable absorbent articles of the invention.

The material of a discrete component may include more than one printed block 80. When the material includes two or more printed blocks 80, the Sensor Values of the printed blocks 80 may be used to detect whether the discrete component is missing entirely from an individual diaper 20, misplaced on the diaper 20, folded or placed in skewed relationship to the other components of the diaper 20. FIGS. 11 and 12 show representative examples of attachment panels 66 that may be used in conjunction with the disposable absorbent articles of the invention. In FIG. 11, the cross-hatched areas represent the locations of three separate printed blocks 80. Two of the printed blocks 80 are located in the same lateral position 82 on one side of the attachment panel 66 (in the corners) and the third printed block 80 covers the full length of the attachment panel 66 in the longitudinal direction 38 near the edge of the attachment panel 66 on the opposite side. The configuration of printed blocks 80 illustrated in FIG. 11 may be used to detect attachment panels 66 that are misplaced on the diaper 20 or that are missing completely. In FIG. 12, the cross-hatched areas represent the locations of four separate printed blocks 80. Two of the printed blocks 80 are located in the same lateral position 82 on one side of the attachment panel 66 (in the corners) and the other two printed blocks 80 are located in the same lateral position 82 on the other side of the attachment panel 66 (in the other two corners). The configuration of printed blocks 80 illustrated in FIG. 12 may be used to detect attachment panels 66 that are folded or skewed on the diaper 20.

The printed block 80 may be formed on the material of a discrete component by using conventional printing techniques. When the material is a nonwoven material, the printed block 80 may be formed by printing an opaque ink in the desired location. Desirably, the ink is applied so that the fibers of the nonwoven material are coated by the ink in sufficient concentration that the desired Printed Block Sensor Value may be achieved.

In addition to including one or more printed blocks 80, the discrete component may include a continuous detector material. The continuous detector material may be incorporated within the material from which the discrete component is made or the continuous detector material may be applied to the surface(s) of the discrete component. The continuous detector material may be a material that is able to effectuate a magnetic continuity, an electrical continuity, and electromagnetic continuity or any combination of such continuities. The continuous detector material may be any material or may take any form that is capable of performing as a registration marker in known registration and controlled placement systems. For example, the continuous detector material may be an optical brightener material that is selected to be sensitive to ultraviolet (UV) radiation. The optical brightener may, for example, be capable of absorbing UV radiation and then fluorescing to emit visible light spectra that can be sensed by an optical detector. UV radiation is generally understood to include electromagnetic radiation having wave lengths ranging from about 20 to about 400 nanometers. The optical brightener material may also be selected to be sensitive to other wavelengths of radiation, such as infrared (IR) radiation.

In one aspect of the present invention, a continuous detector material such as an optical brightener material may be incorporated into the material from which the attachment panel 66 is formed. In another example, the continuous detector material may be incorporated into the material from which the nonwoven layer of the outer cover 42 laminate is formed. With regard to the example of the attachment panel 66, the attachment panel 66 may be formed from a PUB nonwoven material of the type that is described in U.S. Pat. No. 5,858,515 issued to Stokes et al. on Jan. 12, 1999. The fibers used to form the PUB nonwoven material may have a fiber diameter of from about 15 to about 32 microns which may be used to form a material having a basis weight of from about 1.0 to about 2.5 ounces per square yard. The PUB nonwoven material may be formed from polymer pellets that are extruded into the fibers used to form the pattern-unbonded material. In order to incorporate the continuous detector material uniformly throughout the PUB nonwoven material, the continuous detector material may be introduced in pellet or other suitable form to the extruders being used to form the nonwoven fibers. More specifically, polypropylene pellets having a dispersed optical brightener material may be added at a desired weight percentage into the feed hopper of the extruder. By adding the optical brightener to the extruder along with the polymer pellets, the optical brightener is uniformly distributed throughout the fibers that will be formed into the PUB nonwoven material. In order to provide a sufficient level of ultraviolet fluorescence, the optical brightener may be incorporated at a level that results in the optical brightener having a concentration of from about 0.5% to 2.5% in the PUB nonwoven material. By uniformly distributing the continuous detector material throughout the raw material used to form the discrete component, a cost advantage may be, achieved. The attachment panel 66 may also be formed of the PUB nonwoven material when the attachment panel 66 includes a printed block 80 without a continuous detector material.

The concentration of the continuous detector material that is incorporated into the nonwoven material from which the discrete component is formed may be varied depending on the basis weight of the nonwoven material. For example, if a nonwoven material has a more open fiber structure, a higher concentration of continuous detector material may be desirable. The same is true for the formation of printed blocks 80. The more open the fiber structure of the nonwoven material, the higher the concentration of the ink that may be used to form the printed block 80. In order to improve the precision of the registration/controlled placement system and in order to reduce waste, it is desirable that the basis weight of the nonwoven material be as consistent as possible. When the basis weight of the nonwoven material is consistent, the presence of the printed block 80 and continuous detector material may be more consistent and more readily detectable. The discrete component may also include a masking block 68. The masking block 68 may include a space or area of the discrete component for which the ultraviolet (or other type of) fluorescence is covered up or "masked". As a result, the masking block 68 acts as a detectable discontinuity to the continuous detector material in the discrete component. In one aspect of the invention, the masking block 68 may be formed by an area of ink that is printed onto the discrete component. The ink may be applied to form the masking block 68 in such a way so as to have a pigment density resulting in a sensor reading (such as from a luminescence detector described later herein) that is approximately one-fifth of the sensor reading for the non-masking block areas of the discrete component. By applying an ink that reduces fluorescence by about 80%, process variability may be accounted for. The masking block 68 may either be visible or invisible to they eye in the finished discrete component and diaper 20. With regard to the example of an attachment panel 66 formed of a PUB nonwoven material including an optical brightener, the masking block 68 (representatively depicted in FIG. 1 and FIG. 3) may include a block of ink that masks the presence of the optical brightener by about 80% in order to provide consistent detection by a sensor. More specifically, the masking block 68 may include a nitrocellulose resin ink including a titanium dioxide pigment (i.e. a white ink). Desirably, the white ink of the masking block is present in sufficient concentration or opacity to diminish or cover up the presence of the optical brightener. The disposable absorbent articles of the invention may include both a printed block 80 and the combination of a continuous detector material and a masking block 68.

In order to illustrate how a masking block 68 of the invention may diminish the presence of a continuous detector material, a series of measurements were made. The relative masking of the fluorescence of an optical brightener material incorporated into the fibers from which a nonwoven material is formed may be seen by measuring the fluorescence of the "background" portion of a discrete component and the fluorescence of a masking block 68 area that is printed with ink. Considering the values provided in Table 1. below, the measured fluorescence decreases to a detectable degree when there is a block of white or colored ink. Ten points were measured showing a significantly higher fluorescence value for the background material compared with the ink block areas as shown in Table 1. below.

TABLE 1

| Sample | Background | White | Red | Orange | Blue |
| --- | --- | --- | --- | --- | --- |
| 1 | 50 | 15 | 13 | 13 | 35 |
| 2 | 48 | 18 | 11 | 16 | 40 |
| 3 | 52 | 17 | 12 | 15 | 39 |
| 4 | 45 | 18 | 12 | 16 | 34 |
| 5 | 44 | 16 | 12 | 15 | 35 |
| 6 | 51 | 18 | 12 | 14 | 34 |
| 7 | 47 | 15 | 10 | 15 | 36 |
| 8 | 45 | 17 | 11 | 13 | 40 |
| 9 | 48 | 16 | 12 | 16 | 32 |
| 10 | 48 | 18 | 12 | 14 | 37 |
| Average | 47.8 | 16.8 | 11.7 | 14.7 | 36.2 |

Thus, masking blocks 68 that include areas of printed ink are capable of sufficiently reducing the fluorescence measurement of a material into which a detector material has been uniformly incorporated.

Like the printed block 80, the masking block 68 may be located on any position within a discrete component. The masking block 68 may be located within a printed graphic or picture 64. The masking block 68 is desirably positioned on the discrete component in such a way that its presence is readily detected by the sensor or sensors that are being used by the registration system. In FIG. 1 and FIG. 3, the masking block 68 is located near an edge forming the perimeter of the attachment panel 66. The size of the masking block 68 may be varied depending on its position on the discrete component and depending on the overall dimensions or size of the discrete component. As described herein, the discrete component on which the masking block 68 is located has a machine direction, as does the diaper 20 into which the discrete component is incorporated. The machine direction is understood to mean the direction that the composite web of materials from which individual articles are formed is traveling during manufacture. Similarly, the cross direction of the composite web of materials and the individual articles is the direction that is generally perpendicular to the machine direction. The masking block 68 may have a minimum or threshold dimension in the machine direction of the diaper 20 and a minimum or threshold dimension in the cross direction of the diaper 20. The minimum machine direction dimension and the minimum cross direction dimension generally represent the size threshold needed to be able to achieve detection of the masking block 68 by currently available sensors and detectors. A theoretical minimum length for the masking block 68 in the machine direction may be calculated by multiplying the speed of the composite web of materials by the reaction time of the sensor. Representative units for the speed of the composite web of materials may be millimeters per milliseconds. The reaction time of the sensor relates to the shortest time that a sensor is able to turn on and off and representative units may be milliseconds. With regard to the disposable absorbent articles of the present invention, the masking blocks 68 may have a length in the machine direction of the diaper 20 of at least 3 millimeters. With regard to the examples presented in FIGS. 1-3 and 10-12, the machine direction corresponds to the longitudinal direction 38 of the diaper 20 and the cross direction corresponds to the lateral direction 40 of the diaper 20. The printed blocks 80 of the invention may also have a minimum length in the machine or longitudinal direction 38 of the diaper 20. For example, the printed blocks 80 may have a length in the longitudinal direction of the diaper 20 of at least 3 millimeters, determined by the same calculation as that used for the same dimension of the masking block 68.

A theoretical minimum length for the masking block 68 in the cross direction of the diaper 20 may be calculated by determining the sum of the sensor beam spot diameter, the maximum slit position variability and the estimated web weave. The sensor beam spot diameter is the diameter of the detection beam of the sensor being used; essentially, the diameter of the sensor beam spot must fit within (be smaller than) the masking block 68 in order for the sensor to be able to detect the masking block 68. With regard to the representative example of the discrete component being an attachment panel 66, the slit position variability relates to the total possible variation in the distance of the printed masking block 68 from a cross direction edge of the attachment panel 66. For example, if the precision of the location of the printed masking block 68 from a cross direction edge of the attachment panel 66 web of PUB nonwoven material is plus/minus 3 millimeters, the slit position variability would be 6 millimeters. The estimated web weave is the cross direction movement of the composite web of materials in the manufacturing line. While it is desirable to minimize the web weave of the composite web of materials, the web weave can not be completely eliminated. Representative units for the estimated web weave may be millimeters. With regard to the disposable absorbent articles of the invention, the masking block 68 may have a length in the cross direction of the diaper 20 of at least thirteen (13) millimeters. As described above, the cross direction of the diaper 20 corresponds to the lateral direction 40 depicted in the Figures. As with the minimum length in the longitudinal direction 40, the printed blocks 80 of the invention may also have a minimum length in the lateral direction 40 that is determined using the same calculation as that used for the lateral dimension of the masking blocks 68. The printed blocks 80 of the invention may have a length in the lateral direction 40 of at least fifteen (15) millimeters.

The attachment panel 66 representatively shown in FIG. 1 includes the masking block 68 being located near, but separate from an edge of the attachment panel 66. In this example, a sensor or detector used to locate the masking block 68 on the attachment panel 66 material will turn "on" and "off" two times during the time frame that the attachment panel 66 is applied to the diaper 20 and is severed from the attachment panel 66 material web. When the machine direction of the manufacturing process corresponds to the longitudinal direction 38 of the diaper 20, a sensor will turn "on" at the beginning or leading edge of the attachment panel 66 and the sensor will turn "off" at the beginning or leading edge of the masking block 68. The sensor will turn "on" a second time at the trailing edge of the masking block 68 and the sensor will turn "off" at the trailing edge of the attachment panel 66.

As described herein, disposable absorbent articles including registered graphics printed on film materials have been commercially available. The printed film materials include films used to form liquid barrier of the outer cover laminate and films used to form components of attachment panels for both adhesive tape and mechanical fasteners. With regard to an aspect of the present invention, the discrete component includes a material that has a three-dimensional surface topography and that is porous. An example of a category of suitable materials is nonwoven materials. When a printed block 80 or a masking block 68 is printed onto the surface of a nonwoven material, such as a PUB nonwoven material, the individual fibers of the nonwoven material are desirably coated with the ink used to form the printed block 80 or the ink used to form the masking block 68. Additionally, the printing of the printed blocks 80 and the masking blocks 68 desirably also compensates for the porosity of the nonwoven material and the extent to which the inks may pass through the network of fibers of which the nonwoven material is formed.

Figure 8:
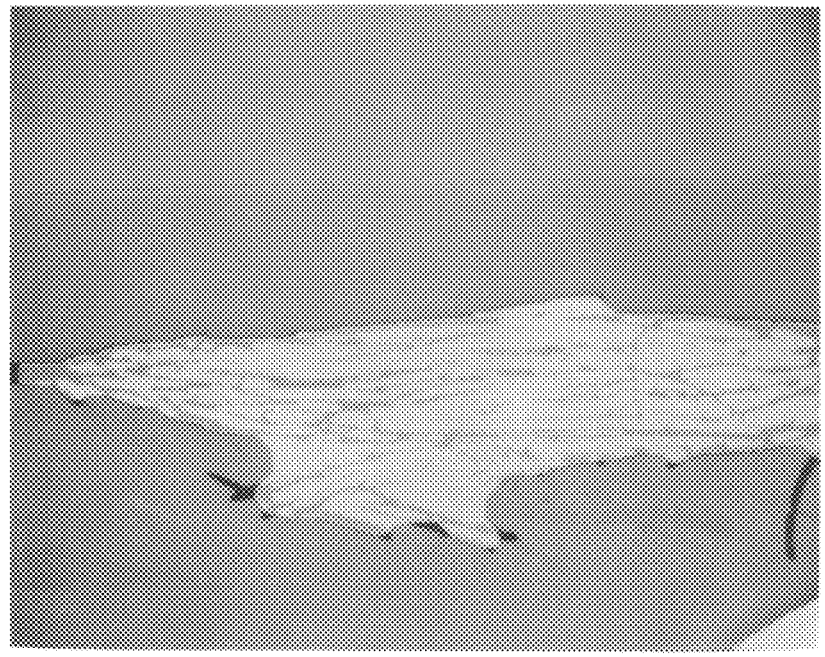
FIG. 8 representatively shows a photomicrograph of a cross-section of a pattern-unbonded nonwoven material prepared by the BSE/HICON method described herein (approximately 27× magnification) in which the detected image is "filled"
Figure 9:
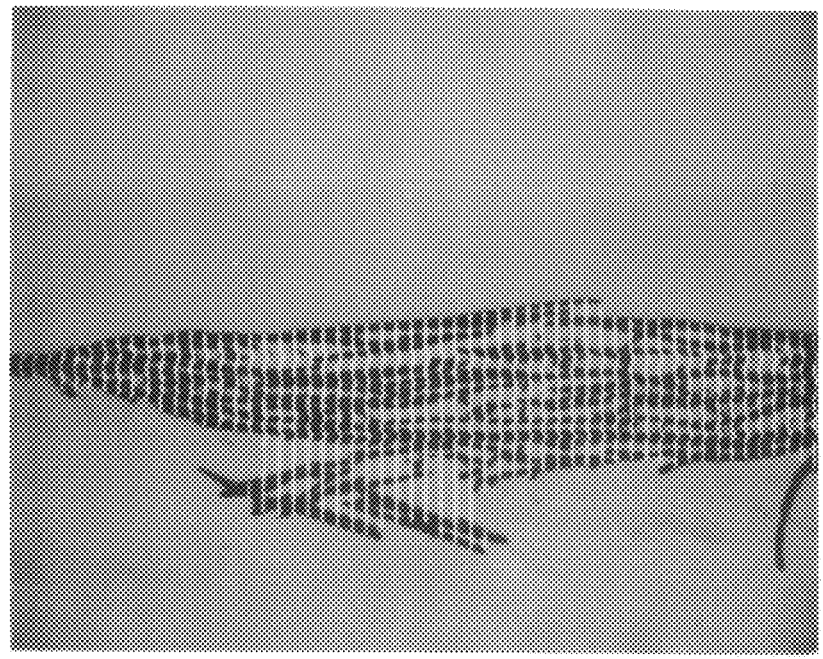
FIG. 9 representatively shows the photomicrograph depicted in FIG. 8 in which the image was "<anded>" (a Boolean operation) with a file containing vertical lines.

In order quantitatively to characterize the three-dimensional topography of the surface of various, representative materials (including nonwoven materials), a technique descriptively entitled "Surface Topographic Variance" has been developed. The discrete components of the present invention onto which the printed blocks 80 and masking blocks 68 are printed may be characterized by their Surface Topographic Variance values. Generally speaking, the Surface Topographic Variance technique measures topographic structure based on cross-sectional views of gossamer fibrous materials. Differences in cross-sectional topographic structure are quantified through determination of the standard deviation of the "side view" topographic histograms, with surface topographic variance being derived from both sides concurrently. In order to prepare cross-sectional microphotographs of the gossamer fibrous materials, a known method, BSE/HICON, was used. The BSE/HICON method is described at Col. 9, line 44 to Col. 13, line 20 of U.S. Pat. No. 5,411,636 issued to Hermans et al. on May 2, 1995. In U.S. Pat. No. 5,411,636, the BSE/HICON method is used to measure a "Debonded Void Thickness" value for tissue. With regard to the present invention, the cross-sections are cut non-randomly through for maximum topographic variance. The technique may be used to prepare the fibrous material samples for further analysis using special software for performing the BSE/HICON method, enabling it to handle a great range of topographic intensity represented by various fibrous materials that may be used in disposable absorbent articles. FIG. 8 and FIG. 9 of the present application representatively illustrate the analysis technique used to determine Surface Topographic Variance values. FIG. 8 shows a photomicrograph (prepared using the BSE/HICON method) of a cross-section of a PUB nonwoven material (approximately 27× magnification) in which the cross-sectional fiber structure is "healed" or "filled" to make a solid detected object. FIG. 9 shows the photomicrograph of FIG. 8 in which the image is "<anded>" (a Boolean operation) with a file containing vertical lines (the line density of which may be similar to that shown in FIG. 9). For the representative nonwoven material, the vertical lines represent topographic samplings at evenly spaced intervals. The length (height) of the vertical lines is then plotted in a histogram. The standard deviation of the histogram provides the Surface Topographic Variance value for the material, having been measured from both sides concurrently.

Figure 4:
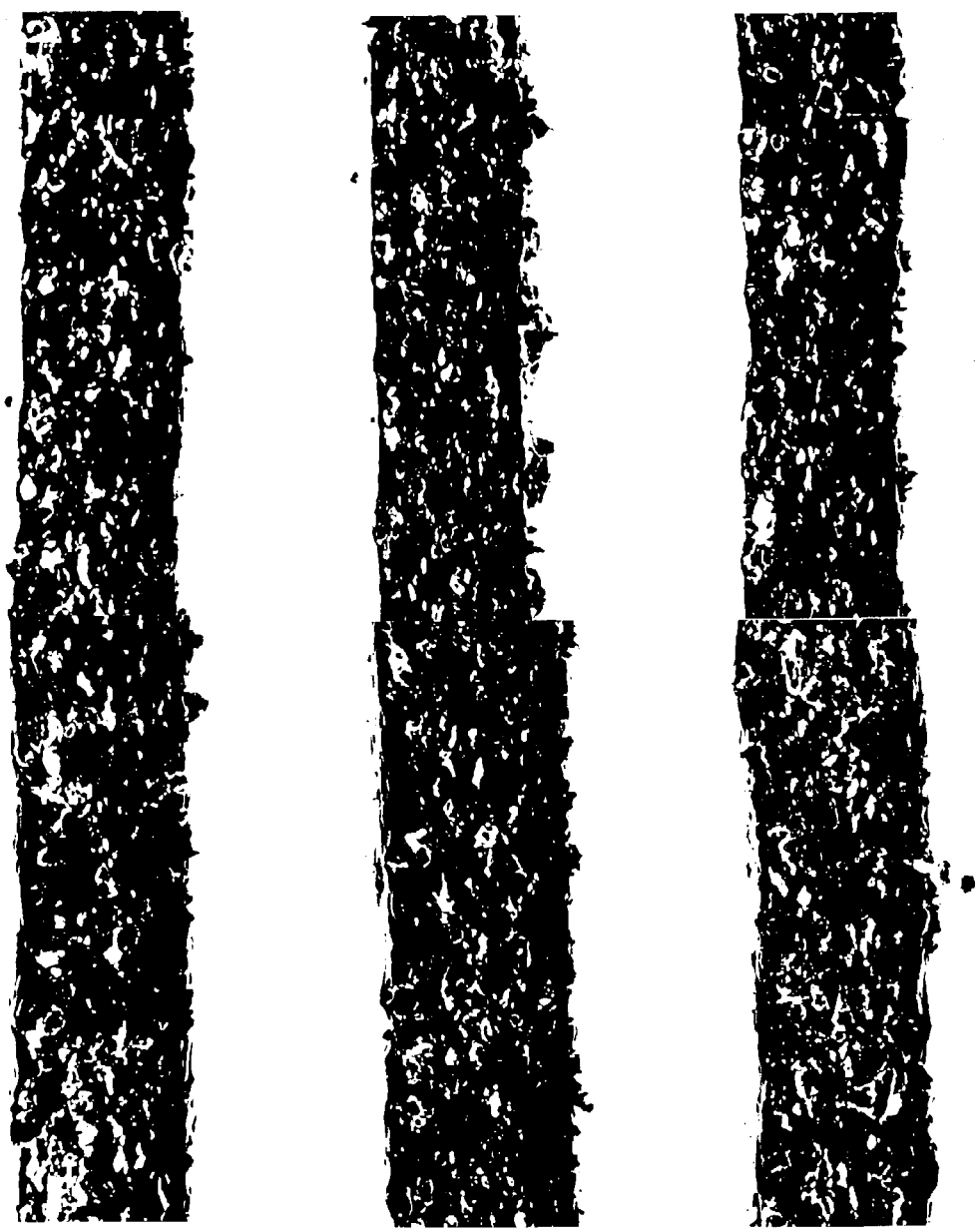
FIG. 4 representatively shows a photomicrograph (prepared by BSE/HICON method) of three cross-sections of a film material at approximately 1200× magnification.
Figure 5:
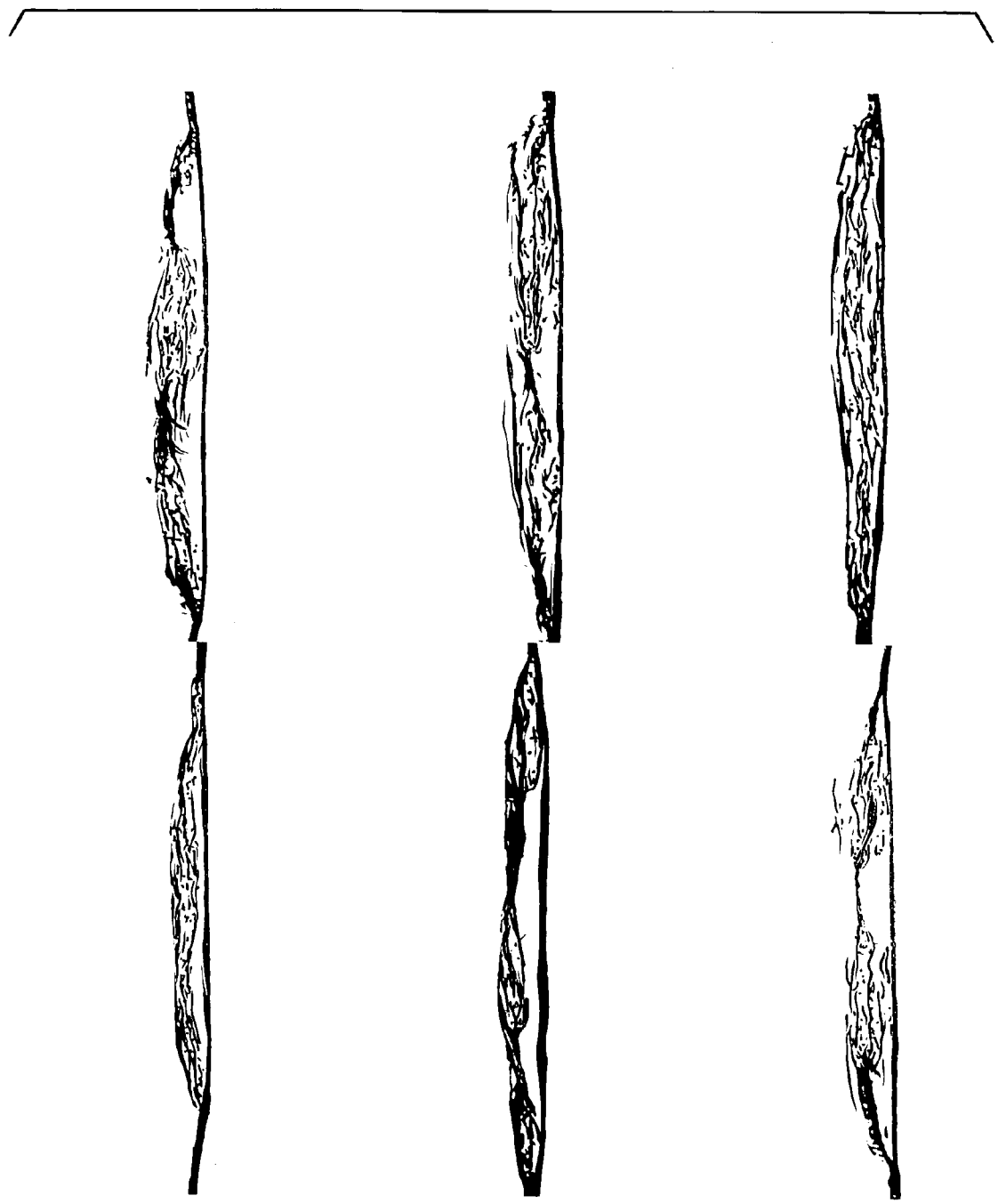
FIG. 5 representatively shows a photomicrograph (prepared by BSE/HICON method) of three cross-sections of a highly-breathable, stretch thermal laminate nonwoven material that may be used to form the outer cover of a disposable absorbent article at approximately 28× magnification.
Figure 6:
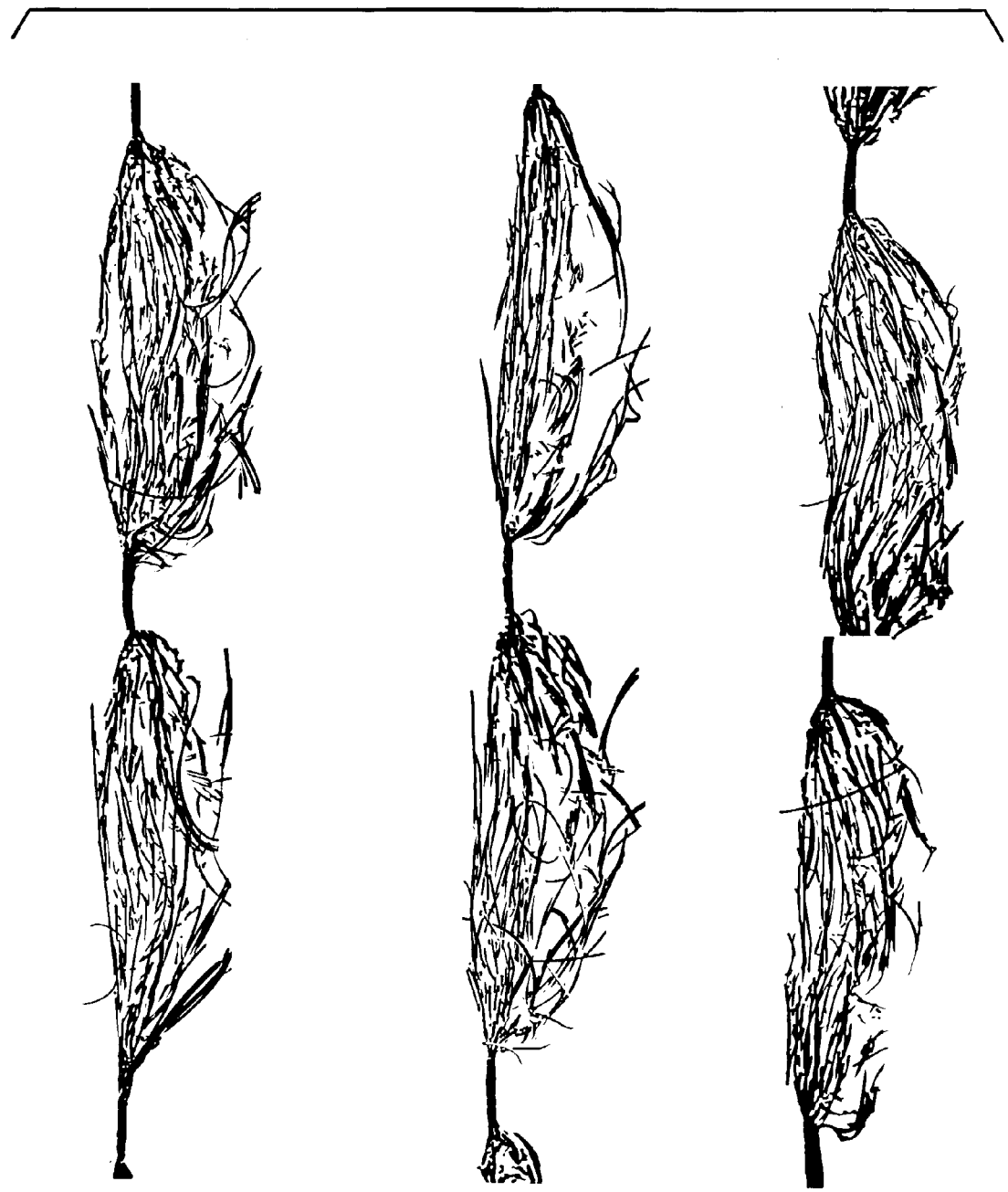
FIG. 6 representatively shows a photomicrograph (prepared by BSE/HICON method) of three cross-sections of a 1.5 osy (ounces per square yard) pattern-unbonded nonwoven material at approximately 20× magnification.
Figure 7:
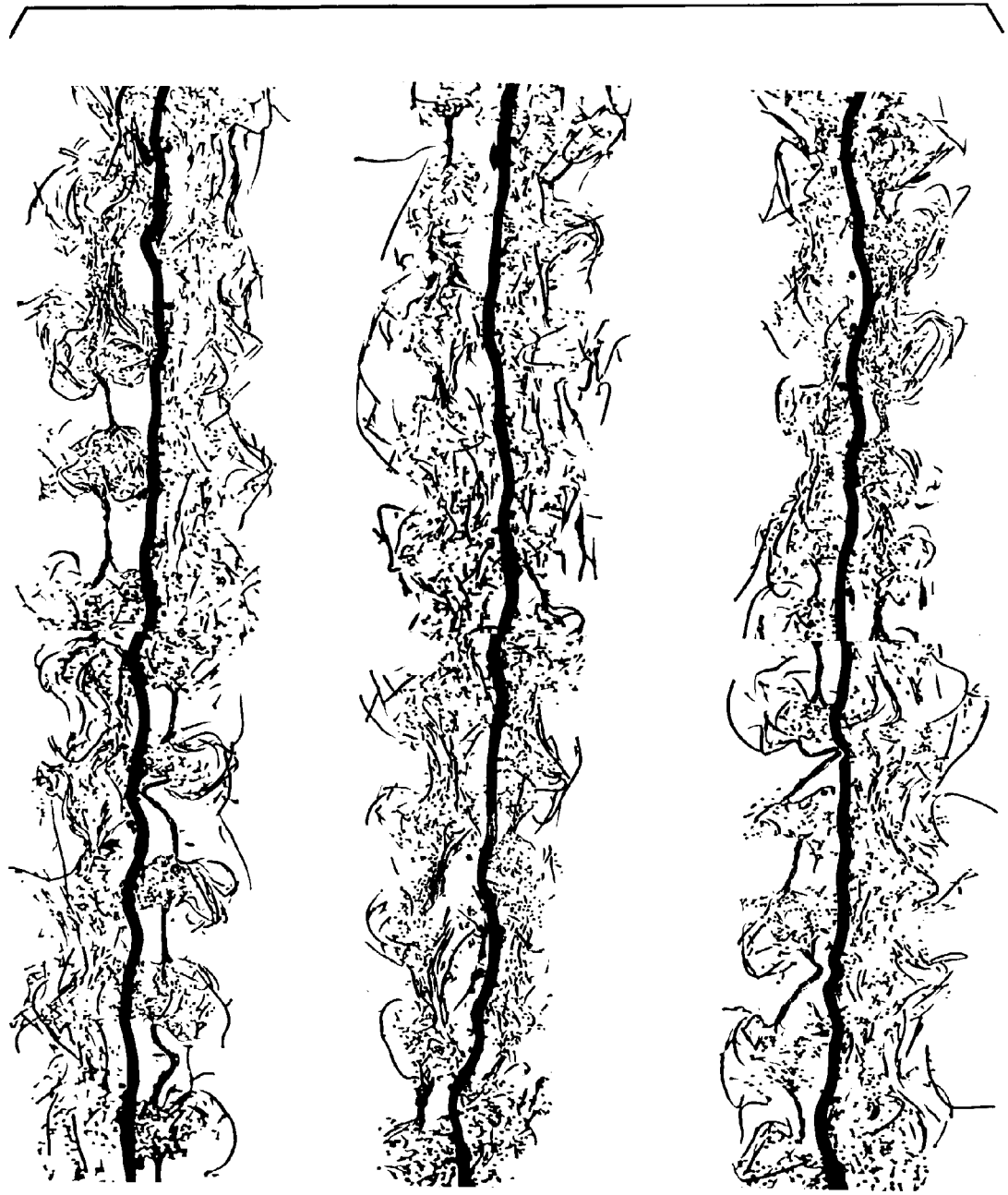
FIG. 7 representatively shows a photomicrograph (prepared by BSE/HICON method) of three cross-sections of a necked-bonded laminate nonwoven material that may be used to form the ears of a disposable absorbent article at approximately 32× magnification.

FIGS. 4-7 include multiple cross-sections for representative materials for which the Surface Topographic Variance was measured. FIG. 4 depicts three cross-sectional photomicrographs (approximately 1200× magnification) of an extensible, breathable film material that is currently used to form the outer cover laminate material for HUGGIES Supreme diapers. A representative film material has the trade designation "XP8600" and may be purchased from Pliant Packaging, located in Newport News, Va. FIG. 5 depicts three cross-sectional photomicrographs (approximately 28× magnification) of a highly-breathable stretch thermal laminate material from which the outer cover 42 of diapers 20 may be formed. This outer cover 42 material may be formed from a breathable film material that is thermally laminated to a nonwoven material, such as a spunbond material. FIG. 6 depicts three cross-sectional photomicrographs (approximately 20× magnification) of a PUB nonwoven material (made of spunbond fibers) from which an attachment panel 66 may be formed. FIG. 7 depicts three cross-sectional photomicrographs (approximately 32× magnification) of a necked bonded laminate material from which the ears 62 of diapers 20 may be formed. The necked bonded laminate material may include two necked substantially crystalline polypropylene spunbond webs and an elastomeric film in between them. The Surface Topographic Variance values determined for the materials depicted in FIGS. 4-7 are provided in Table 2. below.

TABLE 2

| Material Sample | Surface Topographic Variance (micrometers) |
|---|---|
| Film | 1.74 |
| Highly-Breathable Stretch Thermal Laminate | 52.5 |
| Pattern-Unbonded Material | 245 |
| Neck Bonded Laminate | 157 |

The Surface Topographic Variance (standard deviation) determined from this method is a stable and direct measure of topographic variance. The individual histograms for the four material samples are provided below:

Histogram for material in FIG. 4:

```
Cambridge Instruments       QUANTIMET 970       QUIPS/MX: V08.00      USER: K-C
ROUTINE: THVAR2             DATE:               RUN:                  SPECIMEN:
DISTRIBUTION OF FEATURE1 COUNT vs FERET
    Total FEATURE1 COUNT = 555.       Mean = 21.7          Std Dev = 1.74
    Undersize Count = 0.              Oversize Count = 0.
FERET (MICRONS)
    LIMITS       COUNT
    0.-4.00         0. :
    4.00-8.00       0. :
    8.00-12.00      0. :
    12.00-16.00     0. :
    16.00-20.00    94. :1, 1, 1, 1, 1, 1, 1, 1
    20.00-24.00   402. :1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1
    24.00-28.00    59. :1, 1, 1, 1, 1
    28.00-32.00     0. :
    32.00-36.00     0. :
    36.00-40.00     0. :
    40.00-44.00     0. :
    44.00-48.00     0. :
    48.00-52.00     0. :
    52.00-56.00     0. :
    56.00-60.00     0. :
```

Histogram for material in FIG. 5:

```
Cambridge Instruments       QUANTIMET 970       QUIPS/MX: V08.00      USER: K-C
ROUTINE: THVAR2             DATE:               RUN:                  SPECIMEN:
DISTRIBUTION OF FEATURE1 COUNT vs FERET
    Total FEATURE1 COUNT = 324.       Mean = 257.          Std Dev = 52.5
    Undersize Count = 0.              Oversize Count = 0.
FERET (MICRONS)
    LIMITS       COUNT
    0.-30.00        0. :
    30.00-60.00     0. :
    60.00-90.00     0. :
    90.00-120.00    3. :1
    120.00-150.00  10. :1, 1, 1
    150.00-180.00   9. :1, 1, 1
    180.00-210.00  17. :1, 1, 1, 1, 1
```

-continued

| | | |
|---|---|---|
| 210.00-240.00 | 100. | :1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1 |
| 240.00-270.00 | 49. | :1, 1, 1, 1, 1, 1, 1, 1, 1, 1, 1, 1, 1, 1, 1, 1, 1 |
| 270.00-300.00 | 52. | :1, 1, 1, 1, 1, 1, 1, 1, 1, 1, 1, 1, 1, 1, 1, 1, 1, 1 |
| 300.00-330.00 | 62. | :1, 1, 1, 1, 1, 1, 1, 1, 1, 1, 1, 1, 1, 1, 1, 1, 1, 1, 1, 1, 1 |
| 330.00-360.00 | 14. | :1, 1, 1, 1, 1 |
| 360.00-390.00 | 8. | :1, 1, 1, |
| 390.00-420.00 | 0. | : |
| 420.00-450.00 | 0. | : |

Histogram for material in FIG. 6:

Cambridge Instruments  QUANTIMET 970  QUIPS/MX: V08.00  USER K-C
ROUTINE: THVAR2  DATE:  RUN:  SPECIMEN:
DISTRIBUTION OF FEATURE1 COUNT vs FERET
  Total FEATURE1 COUNT = 503.  Mean 938.  Std Dev = 245.
  Undersize Count = 0.  Oversize Count = 0
FERET (MICRONS)

| LIMITS | COUNT | |
|---|---|---|
| 0.-100.00 | 0. | : |
| 100.00-200.00 | 0. | : |
| 200.00-300.00 | 0. | : |
| 300.00-400.00 | 11. | :1, 1, 1, 1 |
| 400.00-500.00 | 22. | :1, 1, 1, 1, 1, 1, 1, 1, 1 |
| 500.00-600.00 | 20. | :1, 1, 1, 1, 1, 1, 1 |
| 600.00-700.00 | 37. | :1, 1, 1, 1, 1, 1, 1, 1, 1, 1, 1, 1, 1, 1, 1 |
| 700.00-800.00 | 51. | :1, 1, 1, 1, 1, 1, 1, 1, 1, 1, 1, 1, 1, 1, 1, 1, 1, 1, 1, 1 |
| 800.00-900.00 | 53. | :1, 1, 1, 1, 1, 1, 1, 1, 1, 1, 1, 1, 1, 1, 1, 1, 1, 1, 1, 1, 1 |
| 900.00-1000.00 | 86. | :1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1 |
| 1000.00-1100.00 | 84. | :1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1 |
| 1100.00-1200.00 | 56. | :1, 1, 1, 1, 1, 1, 1, 1, 1, 1, 1, 1, 1, 1, 1, 1, 1, 1, 1, 1, 1 |
| 1200.00-1300.00 | 64. | :1, 1, 1, 1, 1, 1, 1, 1, 1, 1, 1, 1, 1, 1, 1, 1, 1, 1, 1, 1, 1, 1, 1, 1 |
| 1300.00-1400.00 | 19. | :1, 1, 1, 1, 1, 1, 1 |
| 1400.00-1500.00 | 0. | : |

Histogram for material in FIG. 7:

Cambridge Instruments  QUANTIMET 970  QUIPS/MX: V08.00  USER: K-C
ROUTINE : THVAR2  DATE:  RUN:  SPECIMEN:
DISTRIBUTION OF FEATURE1 COUNT vs FERET
  Total FEATURE1 COUNT = 557.  Mean = 841.  Std Dev = 157.
  Undersize Count = 0.  Oversize Count = 0.
FERET (MICRONS)

| LIMITS | COUNT | |
|---|---|---|
| 0.-100.00 | 0. | : |
| 100.00-200.00 | 0. | : |
| 200.00-300.00 | 0. | : |
| 300.00-400.00 | 0. | : |
| 400.00-500.00 | 2. | : |
| 500.00-600.00 | 31. | :1, 1, 1, 1, 1, 1, 1 |
| 600.00-700.00 | 89. | :1, 1, 1, 1, 1, 1, 1, 1, 1, 1, 1, 1, 1, 1, 1, 1, 1, 1, 1, 1, 1, 1 |
| 700.00-800.00 | 112. | :1, 1, 1, 1, 1, 1, 1, 1, 1, 1, 1, 1, 1, 1, 1, 1, 1, 1, 1, 1, 1, 1, 1, 1, 1, 1 |
| 800.00-900.00 | 103. | :1, 1, 1, 1, 1, 1, 1, 1, 1, 1, 1, 1, 1, 1, 1, 1, 1, 1, 1, 1, 1, 1, 1 |
| 900.00-1000.00 | 135. | :1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1 |
| 1000.00-1100.00 | 54. | :1, 1, 1, 1, 1, 1, 1, 1, 1, 1, 1, 1, 1 |
| 1100.00-1200.00 | 28. | :1, 1, 1, 1, 1, 1, 1 |
| 1200.00-1300.00 | 3. | : |
| 1300.00-1400.00 | 0. | : |
| 1400.00-1500.00 | 0. | : |

The equipment that was used to measure the Surface Topographic Variance values included a QUANTIMET 970 image analysis system (an equivalent system may be used) available from Leica Corporation of Cambridge, England; a 35 mm Nikon lens; a "HM 1212" auto-macro-stage available from Industrial Devices Corporation; a Kreonite Mobil Studio 1 macroviewer; a 70 cm pole position (such that the field of view is one photo); a black background; and four incident flood lights. The software for the method is provided below:

Cambridge Instruments  QUANTIMET 970  QUIPS/MX: V08.00  USER: K-C
ROUTINE: THVAR2  DATE:  RUN:  SPECIMEN:
  AUTH = B. E. KRESSNER
  PURPOSE = MEASURES THICKNESS VARIATION OF Z-PROFILES
  COND = 35 MM ADJ.LENS; 4 FLOODS; PHOTOMONTAGE; POLE POS = 70 CM
  Enter specimen identity
  Scanner (No. 2 Chalnicon LV = 0.00 SENS = 1.56 PAUSE
  SUBRTN STANDARD
  Load Shading Corrector (pattern - LINERO)

```
Calibrate User Specified (Cal Value = 4.585 microns per pixel
FLAG3   := 3.
Pause Message
        Please Position Sample
Pause
Image SAVED (Binary, Res=1 Horiz=1, Vert=1,)
Binary Output goes to SAVED
Image Transfer from file <VERTLN> to Binary Output
Binary Output goes to DETECTED
For MONTAGE = 1 to 2
STAGEX   := 3000.
STAGEY   := 3000.
Stage Move (STAGEX,STAGEY)
Stage Scan      (               X               Y
                scan origin     STAGEX          STAGEY
                field size      110000.0        90000.0
                no of fields    2               3 )
Pause
For FIELD
Clear Binary Output
Scanner (No. 2 Chalnicon LV= 0.00 SENS= 1.60)
Live Frame is Rectangle (X: 106, Y: 34, W: 675, H: 642,)
Image Frame is Rectangle (X: 12, Y: 15, W: 860, H: 668,
Detect 20 ( Darker than 32, Delin )
Amend   (OPEN by 0)
Amend   (CLOSE by 10)
Image Transfer from Binary B <FILL HOLES> to Binary Output
Amend   (OPEN by 9)
Amend   (CLOSE by 25)
Image Transfer from Binary B <FILL HOLES> to Binary Output
Edit (pause) EDIT
Measure Feature   AREA     PERIMETER     FERET 90    X.FCP
                  Y.FCP    YCENTROID
    into array FEATURE (of 200 features and 7 parameters)
YCENT  := Field sum of FEATURE   YCENTROID
YCENT  := YCENT * CAL.CONST
Binary Input B is SAVED
Image Transfer from A <AND> B to Binary Output
Binary Input B is DETECTED
Measure Feature   AREA     PERIMETER     FERET 90    X.FCP
                  Y.FCP    YCENTROID
    into array FEATURE1 (of 500 features and 7 parameters)
FEATURE1   YCENTROID      := YCENTROID * CAL.CONST - YCENT
Accept FEATURE1 FERET from 300. to 1500.
Distribution of COUNT v FERET ( Units MICRONS )
        from FEATURE1 in HISTO1 from 0. to 1500.
        in 15 bins (LIN)
Distribution of COUNT v YCENTROID (Units MICRONS )
        from FEATURE1 in HISTO2 from-450.0 to 450.0
        in 15 bins (LIN)
Stage Step
Next FIELD
Pause Message
PLEASE SELECT ANOTHER MONTAGE, OR FINISH
Pause
Next
Print " "
Print Distribution (HISTO1 differential, bar chart, scale= 0.00)
Print " "
Print " "
Print Distribution ( HISTO2, differential, bar chart, scale= 0.00)
Print " "
For LOOPCOUNT = 1 to 9
Print " "
Next
END OF PROGRAM
```

Representative Registration System

The absorbent articles of the invention may be made using known manufacturing equipment and methods. In one aspect of the present invention, the printed block 80 and the combination of the continuous detector material and the masking block 68 may be used to register graphics or pictures that are printed onto the surface of a discrete component. In another aspect of the present invention, the printed block 80 and the combination of the continuous material and the masking block 68 may be used to register the location of the discrete component in relation to other components of the absorbent article. Regardless of how the printed block 80 and the continuous detector material/masking block 68 combination are utilized, the presence and location of the printed block 80 by itself or the presence and location of the masking block 68 relative to the continuous detector material may be determined using known detection and control systems. Additionally, the presence and location of the printed block 80 by itself or the presence and location of the masking block 68 relative to the continuous detector material may be continuously updated and reacted to using known process control systems and methods. The following is a description of an exemplary, known detection and control system that may be used for such purposes. For purposes of this example, the detection and control system will be described in relation to manufacture of a diaper 20 (as a representative absorbent article) onto which an attachment panel 66 (as a representative discrete component) is registered.

In a particular aspect of the present invention, the continuous detector material is an optical brightener that is constructed to be sensitive to ultraviolet (UV) radiation. As described previously, a continuous detector material that fluoresces at other wavelengths of light (e.g. infrared) may be used. The optical brightener may, for example, be capable of absorbing UV radiation and then fluorescing or emitting visible light in the visible spectra that can be sensed by an optical detector. UV radiation is generally understood to include electromagnetic radiation having wave lengths ranging from about 20-400 nanometers. Suitable optical brighteners include, for example, UVITEX OB manufactured by Ciba-Geigy, and LEUCOPURE EGM manufactured by Sandoz Chemicals Corporation. Other suitable optical brighteners include INTRA WITE OB manufactured by Crompton and Knowles, and PHORWITE K2002 manufactured by Mobay Chemical Company. When the continuous detector material includes UV sensitive optical brightener, the various sensors and detectors may advantageously be provided by a UV activated detector, such as a SICK detector model LUT 1-4 or LUT 3-9 available from SICK OPTIK ELEKTRONIK, INC. a business having offices in St. Paul, Minn. A first sensor, such as a UV or luminescence (e.g. SICK) detector, may be positioned adjacent a moving composite web of materials from which the diapers 20 are formed. The sensor or detector may also be positioned at a point during manufacture after which the web of materials has been separated into individual articles. The luminescence detector directs UV radiation toward the moving composite web and receives visible light signals generated by particular portions and components of the diapers 20 being formed. In particular, as the composite web passes by the luminescence detector, the luminescence detector can detect either or both edges of the masking block 68. The luminescence detector generates corresponding electrical signals and the signals are passed to a computer through suitable means, such as electrical conductors or non-electrical conductors (e.g. fiber optics or radio frequency). An alternative detection scheme is a UV illumination system such as a conventional machine vision system using CCD or CMOS cameras. The desired electrical signals and associated data are appropriately stored in a buffer or other suitable storage medium within the computer. Similar to how the luminescence detector detects the presence of a masking block 68 relative to the presence of an optical brightener material, a detector may be used to detect the presence of a printed block 80 by virtue of the printed block 80 having a Printed Block Sensor Value that is about 3.25 times greater than the Background Sensor Value of the material of the attachment panel 66 in the same lateral position 86 as the lateral position 82 of the printed block 80. As previously described herein, suitable sensors are available from Keyence Corporation. The RGB Digital Fiberoptic Sensors available from Keyence Corporation may be calibrated to the printed block 80 when the manufacturing machine is not running (i.e. the composite web is stationary). The sensor feedback may be displayed as a number between 0 and 999; the number "999" would represent the closest "match" to the printed block 80. The sensitivity adjustment (or sensor output threshold) may be set to a value of 650 so that the sensor is only "on" when a Sensor Value of 650 or greater is detected.

To help accurately determine and control the location of the attachment panels 66, the regions of the composite web and the associated diapers 20 that result, the detection and control system may include a feedback device that isolates the material(s) from which individual diapers 20 are formed into fixed intervals. Examples of such feedback devices include a position reference source, such as a line shaft encoder; a resolver; a velocity sensor; a pattern on the web of materials; or a time interval. The feedback device provides machine position reference data which can include either or both of printed block pulse data and masking block pulse data corresponding to the position and presence of an individual selected diaper 20 intended to be separated from the composite web. The printed block pulse data and the masking block pulse data also correspond to a particular position or phase position of attachment panels 66 relative to one another and relative to the diapers 20 being formed and to the composite web. The printed block pulse data and masking block pulse data may have the form of electrical impulse signals. The electrical signals may be routed through suitable electrical conductors or non-electrical conductors to a suitable processing unit, such as computer. A printed block pulse or a masking block pulse is intended to occur one time per diaper length, and is preferably configured to indicate a machine period that corresponds to a single diaper 20. The printed block pulse or the masking block pulse is typically employed to obtain the phase relationships between the various electrical signals and the elements of the system being employed. The feedback device may further include a meter for generating substantially regularly occurring phasing pulses. The feedback device generates approximately 10,000 phasing pulses per line shaft revolution, and thus 10,000 pulses per diaper article 20. The phasing pulses are employed as a "ruler" to measure the phase and position relationships between the various electrical signals, and can be employed to develop desired measurements of the distances between discrete components connected to the composite web. The phasing pulses may be in the form of electrical signals, which are suitably directed to a computer and associated control system through appropriate electrical conductors. An example of a suitable feedback device is a shaft encoder unit such as a Model BEI#H40A-2500-ABZC-4469-LED-EM20-S unit available from BEI Co., a business having offices in Gurnee, Ill.

Depending on the type of discrete component that is being incorporated into the composite web, a plurality of the discrete components may be provided in various forms. For example, when the discrete component is an attachment panel 66, a plurality of attachment panels 66 may be provided in the form of a component web of material that is brought together with the composite web during manufacture. The component web of material (such as that representatively illustrated in FIG. 3) may include a series of interconnected attachment panels 66 that are separated from each other as they are placed in the proper locations on the composite web. Individual attachment panels 66 may include a graphic or picture 64 that is intended to remain intact after the attachment panel 66 is attached to the composite web. The printed block 80 or the combination of the continuous detector material that is incorporated into the material from which the attachment panel 66 is formed and the masking block 68 provide the input to the detector and the feedback device so that the individual attachment panels 66 may be cut from the component web of material at locations that keep the picture or graphic 64 intact.

The same concept applies if the discrete component is the nonwoven component of the outer cover 42, the fasteners 60 or the ears 62.

The timing of when to cut the component web of material so as to provide the discrete component with intact graphics to the composite web is determined based on electrical signals gathered by the detector and pulse data generated by the feedback device. Each feedback device pulse or "count" represents a discrete unit of movement. The position of each identified attachment panel 66 may be tracked by determining the number of feedback device counts that have occurred since the time that the attachment panel 66 and its printed block 80 or masking block 68 have passed by a specific, predetermined point. For example, once a printed block 80 or masking block 68 passes by the point of the detector, the subsequent location of the printed block 80 or the masking block 68 (and its associated attachment panel 66) along the direction of movement of the composite web may be determined by tracking the number of feedback device counts that occur after the printed block 80 or the masking block 68 has passed the detector. As indicated herein, known process control systems may be used to adjust the speed of the component web of material that includes the plurality of attachment panels 66 relative to the speed of the composite web. The known process control systems may rely upon various inputs including the detection signals from the detector and the lengths of the attachment panel 66 and the desired finished diaper 20 as monitored by the feedback device. For example, the number of counts received by the feedback device may be used to predict where the printed block 80 or the masking block 68 and the attachment panel 66 are going to be when the component web of material is going to be cut. Based upon this information, the motors that drive the speed of the material webs may be sped up or slowed down, as required to properly position the printed block 80 or the masking block 68 relative to the equipment that performs the cutting or relative to the velocity of the two registered substrates or components.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A disposable absorbent article having a longitudinal direction and a lateral direction, further comprising:
   a discrete component, wherein the discrete component is part of the absorbent article;
   wherein the discrete component is an outercover which includes a material and the material is a necked bonded laminate material having a Surface Topographic Variance value of at least 125 micrometers;
   wherein the material includes a printed block and a printed picture, the printed block being located in a longitudinal position on the discrete component and in a lateral position on the discrete component; and
   wherein the printed block has a Printed Block Sensor Value and the material has a Background Sensor Value at the same lateral position as the printed block and the ratio of the Printed Block Sensor Value to the Background Sensor Value is at least 3.25 to 1 and wherein the material of the discrete component further includes a continuous detector material and a masking block.

2. The disposable absorbent article of claim 1, wherein the printed block has a Printed Block Sensor Value of at least 650 and the material has a Background Sensor Value of about 200.

3. The disposable absorbent article of claim 1, wherein the printed block has a Printed Block Sensor Value of at least 950 and the material has a Background Sensor Value of about 200.

4. The disposable absorbent article of claim 1, wherein the printed block has a length in the longitudinal direction of the article of at least 3 millimeters.

5. The disposable absorbent article of claim 1, wherein the printed block has a length in the lateral direction of the article of at least 15 millimeters.

6. The disposable absorbent article of claim 1, wherein the material includes two or more printed blocks.

7. A disposable absorbent article having a longitudinal direction and a lateral direction comprising:
   an outer cover having a garment-facing surface;
   a bodyside liner;
   an absorbent core located between the outer cover and the bodyside liner;
   and
   an attachment panel, wherein the attachment panel is located on the garment-facing surface of the outer cover; and wherein the attachment panel includes a nonwoven material and the nonwoven material has a Surface Topographic Variance value of at least 30 micrometers; wherein the nonwoven material of the attachment panel further includes a continuous detector material and a masking block.

8. The disposable absorbent article of claim 7, wherein the nonwoven material has a Surface Topographic Variance value of at least 175 micrometers.

9. The disposable absorbent article of claim 7, wherein the nonwoven material is a pattern unbonded nonwoven material having a Surface Topographic Variance of at least 200 micrometers.

10. The disposable absorbent article of claim 7, wherein the continuous detector material is an optical brightener.

11. The disposable absorbent article of claim 10, wherein the optical brightener has a concentration of from 0.1% to 2.5% in the nonwoven material of the attachment panel.

12. The disposable absorbent article of claim 7, wherein the masking block has a length in the longitudinal direction of the attachment panel of at least 3 millimeters.

13. The disposable absorbent article of claim 7, wherein the masking block has a length in the lateral direction of the attachment panel of at least 13 millimeters.

14. The disposable absorbent article of claim 7, wherein the masking block includes an opaque printed ink.

* * * * *